US009907751B2

(12) United States Patent
Muni et al.

(10) Patent No.: US 9,907,751 B2
(45) Date of Patent: Mar. 6, 2018

(54) COMPOSITION AND METHOD OF USE OF COLCHICINE ORAL LIQUID

(71) Applicant: RxOMEG Therapeutics LLC, Woburn, MA (US)

(72) Inventors: Indu Muni, North Reading, MA (US); Naomi Vishnupad, Reading, MA (US)

(73) Assignee: RxOMEG Therapeutics LLC, Woburn, MA (US)

( * ) Notice: Subject to any disclaimer, the term of this patent is extended or adjusted under 35 U.S.C. 154(b) by 0 days.

(21) Appl. No.: 15/358,621

(22) Filed: Nov. 22, 2016

(65) Prior Publication Data

US 2017/0258715 A1 Sep. 14, 2017

Related U.S. Application Data

(60) Provisional application No. 62/306,232, filed on Mar. 10, 2016.

(51) Int. Cl.
| | | |
|---|---|---|
| *A61K 31/165* | (2006.01) | |
| *A61K 9/08* | (2006.01) | |
| *A61K 47/26* | (2006.01) | |
| *A61K 47/24* | (2006.01) | |
| *A61K 47/10* | (2017.01) | |
| *A61K 47/36* | (2006.01) | |
| *A61K 9/00* | (2006.01) | |
| *A61K 47/12* | (2006.01) | |

(52) U.S. Cl.
CPC .............. *A61K 9/08* (2013.01); *A61K 9/0053* (2013.01); *A61K 31/165* (2013.01); *A61K 47/10* (2013.01); *A61K 47/12* (2013.01); *A61K 47/24* (2013.01); *A61K 47/26* (2013.01); *A61K 47/36* (2013.01)

(58) Field of Classification Search
CPC .................................................... A61K 31/165
USPC ....................................................... 514/625
See application file for complete search history.

(56) References Cited

U.S. PATENT DOCUMENTS

| | | | |
|---|---|---|---|
| 5,668,154 A * | 9/1997 | Fink ..................... | C07D 413/12 514/338 |
| 7,601,758 B1 | 10/2009 | Davis | |
| 7,619,004 B1 | 11/2009 | Davis | |
| 7,820,681 B1 | 10/2010 | Davis | |
| 7,906,519 B2 | 3/2011 | Davis | |
| 7,915,269 B2 | 3/2011 | Davis | |
| 7,935,731 B2 | 5/2011 | Davis | |
| 7,964,647 B2 | 6/2011 | Davis et al. | |
| 7,964,648 B2 | 6/2011 | Davis | |
| 7,981,938 B2 | 7/2011 | Davis | |
| 8,093,297 B2 | 1/2012 | Davis | |
| 8,097,655 B2 | 1/2012 | Davis | |
| 8,440,722 B2 | 5/2013 | Davis | |
| 8,927,607 B1 | 1/2015 | Ducharme | |
| 9,555,029 B2 | 1/2017 | Ducharme | |
| 2003/0055029 A1* | 3/2003 | D'Amato ............... | A61K 31/05 514/182 |
| 2014/0107213 A1 | 4/2014 | Davis | |
| 2015/0057359 A1 | 2/2015 | Ducharme | |
| 2015/0094317 A1 | 4/2015 | Ducharme | |
| 2015/0094318 A1 | 4/2015 | Ducharme | |
| 2015/0094322 A1* | 4/2015 | Riel ..................... | A61K 9/2009 514/275 |
| 2015/0094375 A1 | 4/2015 | Ducharme | |
| 2015/0164831 A1 | 6/2015 | Roberts et al. | |
| 2015/0196513 A1 | 7/2015 | Nidorf | |
| 2015/0196514 A1 | 7/2015 | Nidorf | |
| 2016/0354396 A1* | 12/2016 | Mahoney ............. | A61K 31/704 |

FOREIGN PATENT DOCUMENTS

| | | |
|---|---|---|
| CN | 102872181 A | 1/2013 |
| WO | WO 2008/021666 A2 | 2/2008 |
| WO | WO 2009/133431 A1 | 11/2009 |
| WO | WO 2013/149109 A1 | 10/2013 |

OTHER PUBLICATIONS

[No Author Listed], Colchicine Injection, USP. Bedford Laboratories. 1999. 2 pages.
[No Author Listed], Colchicine Product Information. Cayman Chemicals. Dec. 5, 2011. 1 page.
[No Author Listed], Colchicine Product Information. Sigma-Aldrich, Inc. 2003. 2 pages.
Artursson et al., Caco-2 monolayers in experimental and theoretical predictions of drug transport. Adv Drug Deliv Rev. Mar. 1, 2001;46(1-3):27-43. Review.
Habib et al., Influence of certain additives on the photostability of colchicine solutions+. Drug Development and Industrial Pharmacy. 1989; 15(11):1905-9.
Rask et al., Cochicine use in 6000 patients with disk disease & other related resistantly-painful spinal disorders. J of Neurolog & Orthopaedic Medicine & Surgery. Dec. 1989; 10(4):291-8.
Stewart et al., Comparison of intestinal permeabilities determined in multiple in vitro and in situ models: relationship to absorption in humans. Pharm Res. May 1995;12(5):693-9.
Yee, In vitro permeability across Caco-2 cells (colonic) can predict in vivo (small intestinal) absorption in man—fact or myth. Pharm Res. 1997; 14(6):763-3.

(Continued)

Primary Examiner — Jennifer M Kim
(74) Attorney, Agent, or Firm — Wolf, Greenfield & Sacks, P.C.

(57) ABSTRACT

Oral liquid colchicine formulations are described herein. Methods of using the oral liquid colchicine formulations are also provided.

11 Claims, 6 Drawing Sheets

(56) References Cited

OTHER PUBLICATIONS

Yu et al., Biopharmaceutics classification system: the scientific basis for biowaiver extensions. Pharm Res. Jul. 2002;19(7):921-5.
International Search Report and Written Opinion for Application No. PCT/US2017/021777 dated Jun. 21, 2017.

* cited by examiner

COMPOSITION AND METHOD OF USE OF COLCHICINE ORAL LIQUID

RELATED APPLICATIONS

This application claims the benefit under 35 U.S.C. § 119 of U.S. provisional application 62/306,232, filed Mar. 10, 2016, the entire contents of which is incorporated herein by reference.

BACKGROUND OF THE INVENTION

Colchicine is an alkaloid compound found in plant extracts that is used to treat gout, familial Mediterranean fever (FMF), pericarditis, Behçet's disease, and atrial fibrillation. Colchicine has also been used to treat amyloidosis, calcium pyrophosphate deposition disease (pseudogout), cirrhosis of the liver, sarcoid arthritis, and inflammatory diseases. Colchicine is administered to patients as a solid oral dosage form, such as a tablet or capsule. A standard dosage of colchicine is typically administered to patients once or twice a day.

Colchicine has previously been shown to be unstable at room temperature in solution. An article published in Drug Development and Industrial Pharmacy, 15(11), 1905-1909 (1989) by Habib, et. al., investigated the stability of colchicine and showed that there is photodegradation of colchicine in solution, especially in the presence of glycerin. Other additives, such as lithium carbonate, p-aminobenzoic acid, and uric acid, used in this study did not prevent the degradation of the colchicine, and furthermore, are not acceptable excipients for an oral solution.

SUMMARY OF THE INVENTION

The invention in some aspects is a method of treating a colchicine sensitive disorder, by orally administering a composition, comprising an oral liquid colchicine formulation to a human subject having a colchicine sensitive disorder in an effective amount to treat the disorder. The colchicine sensitive disorder in some embodiments is selected from gout, familial Mediterranean fever (FMF), pericarditis, Behçet's disease, atrial fibrillation, amyloidosis, calcium pyrophosphate deposition disease (pseudogout), cirrhosis of the liver, sarcoid arthritis, inflammatory diseases, and Disk diseases & related spinal disorders. In some embodiments the oral liquid colchicine formulation is any of the oral liquid colchicine formulations described herein.

The invention in other aspects is a pharmaceutical solution or suspension suitable for oral administration comprising colchicine and a pharmaceutically acceptable solvent system comprised of one or more agents selected from the group consisting of water, glycols, buffering agents, sweeteners, flavoring agents, preservatives and dyes. The buffering agent in some embodiments is about 0.12% (w/v) citric acid (anhydrous). In some embodiments the sweetener is about 0.2% (w/v) sucralose. In other embodiments the flavoring agent is about 0.125% (w/v) artificial grape flavor and/or Flavor Cherry 825.662. In some embodiments the preservative is about 0.3% (w/v) of benzyl alcohol. In some embodiments the preservative is about 0.2% (w/v) of citric acid, anhydrous. In other embodiments the dye comprises one or more of D&C Yellow No. 10 and FD&C Red No. 40. In some embodiments the dye comprises about 0.01% (w/v) FD&C Red No. 40. In some embodiments the thickening agent comprises about 0.15% (w/v) xanthan gum. The concentration of colchicine in the solution in other embodiments is 0.01-1.0 mg/ml or 0.2-0.60 mg/ml.

In other embodiments the pharmaceutically acceptable solvent system is comprised of one or more agents selected from the group consisting of water, propylene glycol, glycerin, benzyl alcohol, parabens, citric acid, xanthan gum, sucralose, a dye, and a flavoring agent and/or taste enhancing agent.

In yet other embodiments the pharmaceutically acceptable solvent system is comprised of the following components:

| Ingredient | % w/v |
|---|---|
| Benzyl Alcohol | 0.3 |
| Citric Acid, Anhydrous | 0.2 |
| Colchicine* | 0.012 |
| FD&C Red No. 40 | 0.01 |
| Dibasic Sodium Phosphate, Heptahydrate | 1.2 |
| Flavor Cherry 825.662 | 0.125 |
| Propylene Glycol | 5 |
| Glycerin | 5 |
| Sucralose | 0.15 |
| Xanthan Gum | 0.15 |
| Water | Q.S. |

*calculated on the anhydrous, solvent free basis

In some embodiments the oral liquid formulations described herein are non-sterile.

In some embodiments the oral liquid formulations comprises compatible and stable preservative. In other embodiments the compatible and stable preservative is benzyl alcohol.

In some embodiments the colchicine formulation has a viscosity in the range of 40-800 cps. In other embodiments the colchicine formulation has a viscosity of 80-250 cps.

In other embodiments the colchicine formulation is volume packaged 60 mL-473 mL, and more preferably 150 ml-300 mL.

The colchicine formulations of the invention may be provided in any type of bottle acceptable for oral liquid medications. In some embodiments the colchicine formulation is packaged in a plastic bottle, such as HDPE (high density polyethylene bottles) or PET. The colchicine solution may also be packaged in glass bottles, which could be amber or clear, in other embodiments. The caps of the bottles may or may not have an induction seal and could be easy to open or tamper resistant. The bottles and/or the packaging could be multi use or single dose units. A preferred embodiment is a 190 ml HDPE container closure system with a cap with an induction seal.

In some embodiments the oral liquid colchicine formulation is stable at room temperature for at least 3 months, at least 6 months, at least 18 months, or at least 24 months. In some embodiments the oral liquid colchicine formulation is stable at accelerated temperatures for at least 1 month, at least 2 months, at least 3 months, or at least 6 months. In some embodiments the oral liquid colchicine formulation is determined to be stable when the solution has less than 5%, less than 4%, less than 3%, less than 2%, less than 1% or less than 0.5% of any one degradant. In other embodiments the oral liquid colchicine formulation is determined to be stable when the solution has less than 5%, less than 4%, less than 3%, less than 2%, less than 1% or less than 0.5% of total degradants. In some embodiments, degradants include β lumicolchicine, γ-lumicolchicine, colchiceine, and any other individual unknown impurities.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF DRAWINGS

The figures are illustrative only and are not required for enablement of the invention disclosed herein.

FIGS. 5A-5B show chromatograms of liquid colchicine dosing (FIG. 5A) and liquid A→B receiver sample (FIG. 5B). FIGS. 5C-5D show chromatograms of colchicine USP tablet dosing (FIG. 5C) and liquid A→B receiver sample (FIG. 5D). FIGS. 5E-5F show chromatograms of colchicine capsule dosing (FIG. 5E) and liquid A→B receiver sample (FIG. 5F).

DETAILED DESCRIPTION

Figure 1:
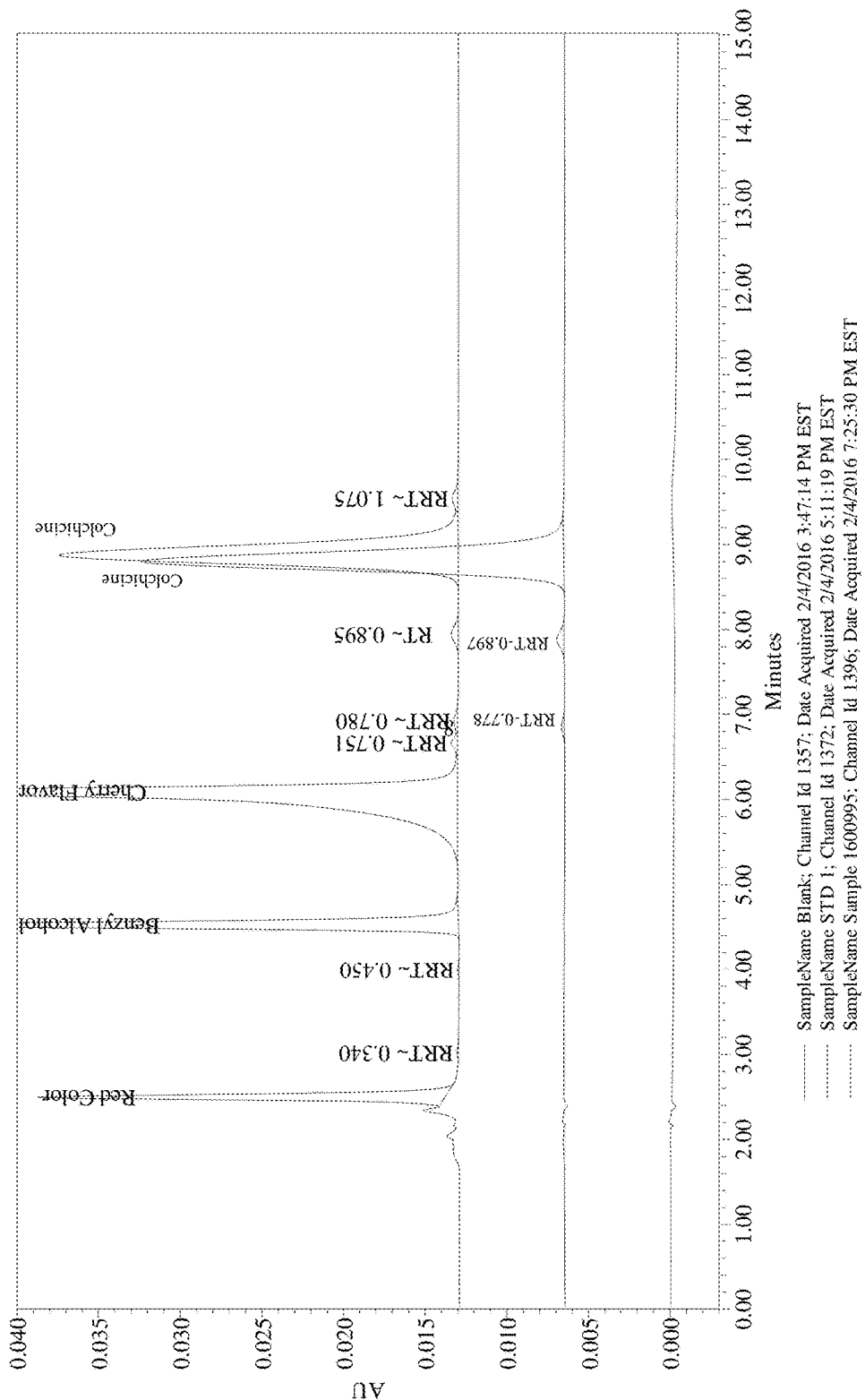
FIG. 1 depicts a chromatograph. Sample, colchicine standard, and diluent blank can be found from top to bottom.

Colchicine is administered to patients as a solid oral dosage form, such as a tablet or capsule. Colchicine has previously been shown to be unstable at room temperature in solution. Habib et al. showed rapid photodegradation of colchicine in solution, especially in the presence of glycerin. Other additives, such as lithium carbonate, p-aminobenzoic acid, and uric acid, were used in this study, but did not prevent the degradation of the colchicine, and furthermore, are not acceptable excipients for an oral solution. Surprisingly, it was found according to the invention, that liquid suspensions or solutions of colchicine formulated as an oral solution are stable at ambient temperature and have stable pH for extended periods of time. For instance the liquid solutions or suspensions described herein are stable for at least three months in refrigerated, ambient, and accelerated temperatures. The findings of the invention have important clinical implications. An oral solution or suspension of colchicine is advantageous for colchicine dosing and administration.

Colchicine, (−)-N-[(7S,12aS)-1,2,3,10-tetramethoxy-9-oxo-5,6,7,9-tetrahydrobenzo[a]heptalen-7-yl]-acetamide, is a pale yellow powder soluble in water in 1:25 dilution. Colchicine is an alkaloid found in extracts of certain plants such as *Colchicum autumnale* and *Gloriosa superba*. Colchicine arrests cell division in animals and plants. It has adversely affected spermatogenesis in humans and in some animal species under certain conditions.

The invention encompasses liquid formulations of colchicine. The present invention provides for liquid formulation of colchicine, suitable for oral administration that is stable at room temperature. The liquid formulation can be either a solution or a suspension. Colchicine solid oral dosage forms, such as tablets and capsules have been used for the prophylactic treatment of gout and to treat patients suffering from gout flares. In addition to treating patients with gout, colchicine is also used to treat patients with Familial Mediterranean Fever (FMF). Studies have also shown that colchicine may be used to treat patients with cardiovascular disease and various other conditions.

Currently colchicine is primarily used to treat patients suffering from gout. An oral liquid formulation can provide physicians more flexibility in designing dosage regimens for their patients. This is particularly important since colchicine is toxic and has a narrow therapeutic index. The methods described herein are useful for the treatment of gout. The treatment of gout involves the prophylactic treatment of gout as well as the treatment of gout flares. The prophylactic treatment of gout refers to the treatment of a patient who has had one or more gout flares, in order to reduce the occurrence of future gout flares.

Some of the challenges in formulating an oral liquid of colchicine include maintaining stability of the colchicine, maintaining an optimum pH, and masking the bitter taste. It is also important to establish an effective preservative system to prevent the growth of bacteria, mold, and other contaminants. Additionally, the oral liquid colchicine must be patient friendly and requires suitable packaging, such as a container closure system that factors in the potential effects of light and air exposure.

Also provided herein are methods of treating gout, familial Mediterranean fever (FMF), Behçet's disease, cardiovascular disease (atrial fibrillation, pericarditis), amyloidosis, calcium pyrophosphate deposition disease (pseudogout), cirrhosis of the liver, sarcoid arthritis, inflammatory diseases, and Disk diseases & related spinal disorders comprising administering to a patient, such as a child or an elderly patient, an oral liquid formulation compounded from colchicine as described herein. In some embodiments, oral liquid formulations disclosed herein can also be used to treat for other conditions (e.g., skin conditions) known in the art (Ben-Chetrit E, Levy M. Colchicine: 1998 update. Semin Arthritis Rheum. 1998; Yurdakul S, Mat C, Tüzün Y, Ozyazgan Y, Hamuryudan V, Uysal O, Senocak M, Yazici H. A double-blind trial of colchicine in Behçet's syndrome. Arthritis Rheum. 2001 November; 44(11):2686-92. August; 28(1):48-59; Molad Y. Update on colchicine and its mechanism of action. Curr Rheumatol Rep. 2002 June; 4(3):252-6).

Commonly, geriatric populations encounter difficulty being administered solid oral dosage forms such as tablets and capsules. This may lead to non-compliance with the recommended pharmacotherapy with the solid oral dosage forms and likely results in rendering the therapy ineffective. Solid oral dosage forms are usually not favorable for geriatric populations due to the potential risk of choking. Additionally, certain solid oral dosage forms of medications cannot be administered simply by crushing (e.g., patients requiring various types of feeding tubes) because of the coating or drug delivery mechanism by which the drug is released.

As used herein, "colchicine" refers to colchicine base, its salt, or solvate or derivative or isomer or polymorph thereof.

Suitable compounds include the free base, the organic or inorganic salts, isomers, isomer salts, solvates, polymorphs, complexes, etc.

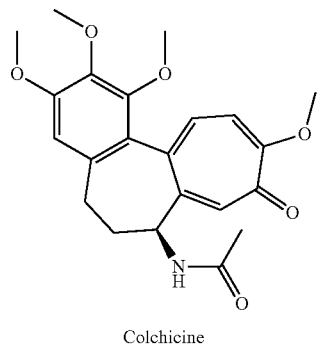 [SMILES: COc1cc2c(c(OC)c1OC)-c1ccc(OC)c(=O)cc1[C@@H](NC(C)=O)CC2]

Colchicine

In some embodiments the oral liquid colchicine formulation is stable at room temperature for at least 3 months, at least 6 months, at least 18 months, or at least 24 months. In some embodiments the oral liquid colchicine formulation is stable at accelerated temperatures for at least 1 month, at least 2 months, at least 3 months, or at least 6 months. In some embodiments the oral liquid colchicine formulation is determined to be stable when the solution has less than 5%, less than 4%, less than 3%, less than 2%, less than 1% or less than 0.5% of any one degradant. In other embodiments the oral liquid colchicine formulation is determined to be stable when the solution has less than 5%, less than 4%, less than 3%, less than 2%, less than 1% or less than 0.5% of total degradants. In some embodiments, degradants include β lumicolchicine, γ-lumicolchicine, colchiceine, and any other individual unknown impurities.

Gout

Gout (or gouty arthritis) is a disease caused by a build-up of uric acid due to an overproduction of uric acid or a reduced ability of the kidney to get rid of uric acid. It is more common in males, postmenopausal women, and people with high blood pressure. Heavy alcohol use, diabetes, obesity, sickle cell anemia, and kidney disease also increase the risk. The condition may also develop in people who take drugs that interfere with uric acid excretion.

In gout, monosodium urate or uric acid crystals are deposited on the articular cartilage of joints, tendons and surrounding tissues due to elevated concentrations of uric acid in the blood stream. This provokes an inflammatory reaction of these tissues. Gout is characterized by excruciating, sudden, unexpected, burning pain, as well as swelling, redness, warmness, and stiffness in the affected joint. Low-grade fever may also be present. The patient usually suffers from two sources of pain. The crystals inside the joint cause intense pain whenever the affected area is moved. The inflammation of the tissues around the joint also causes the skin to be swollen, tender and sore if it is even slightly touched. Acute gouty arthritis (alternatively referred to as a gout flare or a gout attack) is a sudden attack of pain in affected joints, especially in the feet and legs. Chronic gout involves repeated attacks of joint pain.

In acute gouty arthritis, symptoms develop suddenly and usually involve only one or a few joints. The big toe, knee, or ankle joints are most often affected. The pain frequently starts during the night and is often described as throbbing, crushing, or excruciating. The joint appears infected with signs of warmth, redness, and tenderness. The attacks of painful joints may go away in several days, but may return from time to time. Subsequent attacks usually last longer. Some people may progress to chronic gout (chronic gouty arthritis), while others may have no further attacks.

If several attacks of gout occur each year, it can lead to joint deformity and limited motion in joints. Uric acid deposits, called tophi, develop in cartilage tissue, tendons, and soft tissues. These tophi usually develop only after a patient has suffered from the disease for many years. Deposits also can occur in the kidneys, leading to chronic kidney failure.

Colchicine can be used for treating adults with acute gouty arthritis and pain in attacks of acute gouty arthritis, and also can be used beneficially for treating adults with chronic gout for prophylaxis of acute gout flares. Although its exact mode of action in the relief of gout is not completely understood, colchicine is known to decrease the inflammatory response to urate crystal deposition by inhibiting migration of leukocytes, to interfere with urate deposition by decreasing lactic acid production by leukocytes, to interfere with kinin formation and to diminish phagocytosis and the subsequent anti-inflammatory response. The anti-inflammatory effect of colchicine is relatively selective for acute gouty arthritis. However, other types of arthritis occasionally respond. It is neither an analgesic nor a uricosuric and will not prevent progression to chronic gouty arthritis. It does have a prophylactic, suppressive effect that helps to reduce the incidence of acute attacks and to relieve the residual pain and mild discomfort that patients with gout occasionally experienced. In some instances, non-steroidal anti-inflammatory drugs (NSAIDs) may also be prescribed to relieve pain and inflammation in acute gouty arthritis attacks. Strong painkillers, such as codeine, or corticosteroids may also be prescribed to relieve the pain.

Colchicine is rapidly absorbed from the gastrointestinal tract. Peak concentrations occur in 0.5 to 2 hours. The drug and its metabolites are distributed in leukocytes, kidneys, liver, spleen and the intestinal tract. Colchicine is metabolized in the liver and excreted primarily in the feces with 10 to 20% eliminated unchanged in the urine. In some embodiments, oral liquid formulations disclosed herein are used to treat gout.

Familial Mediterranean Fever (FMF)

Familial Mediterranean Fever (FMF) is a recessively inherited disorder characterized by dramatic episodes of fever, serosal inflammation and abdominal pain. This inflammatory disorder is episodic, with self-limited bouts of fever accompanied by unexplained arthritis, sterile peritonitis, pleurisy and/or skin rash. Patients often develop progressive systemic amyloidosis from the deposition of the acute phase reactant serum amyloid A (SAA). In some patients, progressive systemic amyloidosis can lead to kidney failure and death. The factors which incite an episode are unclear. In some embodiments, colchicine can be prescribed as an anti-inflammatory therapy.

FMF is observed primarily in individuals of non-Ashkenazi Jewish, Armenian, Arab and Turkish background. Although rare in the United States, incidence of FMF in Middle Eastern populations can be as high as 1:7 in Armenian populations and 1:5 in non-Ashkenazi Jewish populations.

FMF attacks are characterized by a massive influx of polymorphonuclear leukocytes (PMNs) into the affected anatomic compartment. At the biochemical level, patients have been reported to have abnormal levels of C5a inhibitor (Matzner and Brzezinski, "C5a-inhibitor deficiency in peritoneal fluids from patients with familial Mediterranean fever," *N. Engl. J. Med.*, 311:287-290 (1984)), neutrophil-stimulatory dihydroxy fatty acids (Aisen et al, "Circulating hydroxy fatty acids in familial Mediterranean fever," *Proc. Natl. Acad. Sci. USA*, 2:1232-1236 (1985)), and dopamine β-hydroxylase (Barakat et al, "Plasma dopamine beta-hydroxylase: rapid diagnostic test for recurrent hereditary polyserositis," *Lancet*, 2:1280-1283 (1988)). Although linkage studies have placed the gene causing FMF (designated MEFV) on chromosome 16p (Pras et al., "Mapping of a gene causing familial Mediterranean fever to the short arm of chromosome 16," *N. Engl. J. Med.*, 326:1509-1513 (1992); Shohat et al., "The gene for familial Mediterranean fever in both Armenians and non-Ashkenazi Jews is linked to the α-globin complex on 16p: evidence for locus homogeneity," *Am. J. Hum. Genet.*, 51:1349-1354 (1992); Pras et al, "The gene causing familial Mediterranean fever maps to the short arm of chromosome 16 in Druze and Moslem Arab families," *Hum. Genet.*, 94:576-577(1994); French FMF Consortium, "Localization of the familial Mediterranean fever gene (FMF) to a 250 kb-interval in non-Ashkenazi Jewish founder haplotypes," *Am. J. Hum. Genet.*, 59:603-612 (1996)), the genetic basis of FMF has not previously been identified. In some embodiments, oral liquid formulations disclosed herein are used to treat FMF.

Behçet's Disease

Behcet's disease is a chronic multisystem disease characterized by oral and genital aphthae, arthritis, cutaneous lesions, and ocular, gastrointestinal, and neurologic manifestations. It was first described by the Turkish dermatologist Hulusi Behcet in 1937 as "recurrent oral aphthous ulcers, genital ulcers, and 'hypopyon-uveitis.'" The diagnosis of Behcet's disease is based on clinical criteria as established by O'Duffy and Goldstein and the International Study Group. Complex aphthosis is the presence of almost constant, multiple oral or oral and genital aphthae in the absence of systemic manifestations. These patients must be distinguished from those with Behcet's disease. Colchicine has been used as a treatment for Behcet's disease through its ability to inhibit of neutrophil functions (Hirohata et al., Behçet's disease. Arthritis Res Ther 2003 5:139 DOI: 10.1186/ar757). In some embodiments, oral liquid formulations disclosed herein are used to treat Behçet's Disease.

The prevalence of Behcet's disease is higher in the Middle East and Japan where it is approximately 1 in 1000. The disease is far less common in northern Europe, the United States, and the United Kingdom. The mean age of onset ranges from the mid to late 20s to the fourth decade, according to several series, with a slightly higher male to female ratio. It is relatively rare in children and the elderly. Behcet's disease is also uncommon among black Africans who, when they are affected, tend to have more mucocutaneous features. Although a definitive pattern of inheritance has not been elucidated, familial cases have been reported. Patients with complex aphthosis are probably a subset of patients with recurrent aphthous stomatitis, which is defined as the recurrence of 1 or more painful oral ulcers at intervals ranging from days to months. The prevalence of recurrent aphthosis ranges from 5% to 66%. Onset may occur in childhood or adolescence and some patients experience a decrease in frequency with advancing age. (source: J. V Ghate and J. L. Jorizzo, "Behcet's disease and complex aphthosis", Journal of the American Academy of Dermatology, 1999, 40(1), 1-18.)

Cardiovascular Disease (Atrial Fibrillation, Pericarditis)

Cardiovascular disease (CVD) involves the heart of blood vessels. CVD includes, but is not limited to coronary artery diseases (CAD), stroke, hypertensive heart disease, rheumatic heart disease, cardiomyopathy, atrial fibrillation, congenital heart disease, endocarditis, pericarditis, aortic aneurysms, peripheral artery disease, and venous thrombosis.

One very typical and dangerous arrhythmia is atrial fibrillation (AFIB). AFIB is the most common cardiac arrhythmia resulting in hospitalization in the United States. AFIB is identified by irregular heart rhythms and is clinically defined as uncoordinated contractions of the atria. Patients often experience palpitations and have an increased risk of stroke. Some patients may be asymptomatic. Approximately one-third of all strokes are due to AFIB. Furthermore, the presence of AFIB makes strokes 5-times more likely and 2-times more debilitating.

The role of colchicine in inflammation, microtubule disruption, adhesion of neutrophils, and other qualities, makes it a promising treatment for some cardiovascular diseases (Deftereos et al., Colchicine and the Heart: pushing the envelope. J Am Coll Cardiol. 2013; 62(20):1817-1825. doi:10.1016/j.jacc.2013.08.726; Tong et al., Colchicine in cardiovascular disease: an ancient drug with modern tricks. 2016 Heart doi:10.1136/heartjnl-2015-309211). In some embodiments, oral liquid formulations disclosed herein are used to treat cardiovascular diseases (e.g., atrial fibrillation and pericarditis).

Amyloidosis

Amyloidosis is a rare and potentially fatal disease that can be either localized or systemic. There are four major types of amyloidosis. The four major types include immunoglobulin (primary) amyloidosis, reactive (secondary) amyloidosis, beta-2 microglobulin amyloidosis and hereditary amyloidosis. Each different type of amyloidosis presents a different prognosis and stems from different underlining conditions. The pathologic features of amyloid deposits include beta-pleated sheet structures that are composed of amyloid fibrils with diameters between 8 to 10 nm. B eta-pleated sheets can be viewed under polarized light after being stained using Congo Red stain, these stained fibrils display an apple green birefringence.

Secondary amyloidosis is associated with chronic inflammatory diseases such as FMF. The precursor protein responsible for constructing the amyloid fibrils associated with secondary amyloidosis is serum amyloid A, an acute-phase reactant. Typical sites of amyloid accumulation include the spleen, liver, lymph nodes, adrenal glands, and the kidneys. Symptoms that are nonspecific include complaints of weakness and fatigue. Specific complaints are directly associated to organ involvement, these symptoms commonly include edema and pain. In some embodiments, oral liquid formulations disclosed herein are used to treat amyloidosis.

Calcium Pyrophosphate Deposition Disease (Pseudogout)

Calcium pyrophosphate deposition disease (CPDD), also known as pseudogout, chondrocalcinosis, and pyrophosphate arthropathy, is a rheumatologic disorder with varied symptoms and signs arising from the accumulation of crystals of calcium pyrophosphate dihydrate in the connective tissues.

Pseudogout refers to the acute symptoms of joint inflammation or synovitis: red, tender, and swollen joints that may resemble gouty arthritis. The disorder is more common in older adults. It may be asymptomatic, or it can be associated with osteoarthritis, or it can present as an acute or chronic inflammatory arthritis that causes pain in one or more joints. The white blood cell count is often raised.

The arthritis is usually polyarticular (inflammation of several joints in the body), although it may begin as monoarticular (one joint). CPPD crystals tend to form within articular tissues. Knees are the most commonly affected joints, along with wrists and hips. In rare cases, pseudogout may affect the spinal canal and cause damage to the spinal cord. In some embodiments, oral liquid formulations disclosed herein are used to treat pseudogout.

Cirrhosis of the Liver

Cirrhosis, a condition in which the liver does not function properly due to long-term damage, typically comes on slowly over months or years. Early on, there are often no symptoms. As the disease worsens, a subject may become tired, weak, itchy, have swelling in the lower legs, develop yellow skin, bruise easily, have fluid build-up in the abdomen, or develop spider-like blood vessels on the skin. The fluid build-up in the abdomen may become spontaneously infected. Other complications include hepatic encephalopathy, bleeding from dilated veins in the esophagus or dilated stomach veins, and liver cancer. Hepatic encephalopathy results in confusion and possibly unconsciousness. Colchicine has been shown to have anti-fibrotic effects in relation to hepatic diseases (Leung et al., Colchicine—Update on mechanisms of action and therapeutic uses. 2015. Seminar in Arthritis and Rheumatism. 45 (3), 257-67).

Cirrhosis is most commonly caused by alcohol, hepatitis B, hepatitis C, and non-alcoholic fatty liver disease. Typically, more than two or three drinks per day over a number of years is required for alcoholic cirrhosis to occur. Non-alcoholic fatty liver disease is due to a number of reasons, including being overweight, diabetes, high blood fats, and high blood pressure. A number of less common causes include autoimmune hepatitis, primary biliary cirrhosis, hemochromatosis, certain medications, and gallstones. Cirrhosis is characterized by the replacement of normal liver tissue by scar tissue. These changes lead to loss of liver function. Diagnosis is based on blood testing, medical imaging, and liver biopsy. In some embodiments, oral liquid formulations disclosed herein are used to treat hepatic diseases (e.g., cirrhosis of the liver).

Sarcoid Arthritis

Sarcoidosis, a disease involving abnormal collections of inflammatory cells, can be involved with the joints, bones and muscles. This causes a wide variety of musculoskeletal complaints that act through different mechanisms. Approximately 5-15% of cases affect the bones, joints, or muscles.

Sarcoid arthritis has two classifications: acute or chronic. Sarcoidosis patients with acute arthritis often also accompanies bilateral Hilar lymphadenopathy and Erythema nodosum. Usually true arthritis is not present, but instead periarthritis presents itself as a swelling in the soft tissue around the joints that can be seen by ultrasonographic methods. These joint symptoms tend to precede or occur at the same time as erythema nodosum develops. Enthesitis also occurs in about one-third of patients with acute sarcoid arthritis, mainly affecting the Achilles tendon and heels. Soft tissue swelling at the ankles can be prominent, and biopsy of this soft tissue reveals no granulomas, but does show panniculitis that is similar to erythema nodosum.

Chronic sarcoid arthritis usually occurs in the setting of more diffuse organ involvement. The ankles, knees, wrists, elbows, and hands may all be affected in the chronic form and often in a polyarticular pattern. Dactylitis similar to that seen in Psoriatic arthritis, that is associated with pain, swelling, overlying skin erythema, and underlying bony changes may also occur. In some embodiments, oral liquid formulations disclosed herein are used to treat sarcoid arthritis.

Disk Diseases & Related Spinal Disorders

Disk diseases & related spinal disorders are a group of disorders that are quite painful. It is believed that colchicine acts directly on diskal inflammation to reduce inflammation in the area surrounding the spinal nerve roots. Colchicine has also been shown to cause an increase of endorphin-producing neurons in the spinal cord and to prevent deposition of amyloid in damaged disk. In some embodiments the subject has diskal back pain and or sciatica. In some embodiments, oral liquid formulations disclosed herein are used to treat disk diseases and related spinal disorders.

Formulations

The liquid formulations described herein may include additional ingredients. For instance these additional components may include, but are not limited to, buffering agents, preservatives, sweeteners, flavoring agents, glycols such as propylene glycol and glycerin, as examples, and coloring agents. Additional excipients such as tonicity agents and chelating agents are within the scope of the embodiments.

Buffering agents maintain the pH when colchicine is compounded into a liquid form. Non-limiting examples of buffering agents include, but are not limited to, sodium bicarbonate, potassium bicarbonate, magnesium hydroxide, magnesium lactate, magnesium gluconate, aluminum hydroxide, aluminum hydroxide/sodium bicarbonate precipitate, a mixture of an amino acid and a buffer, a mixture of aluminum glycinate and a buffer, a mixture of acid salt and an amino acid and a buffer, and a mixture of an alkali salt of an amino acid and a buffer. Additional buffering agents include citric acid, sodium citrate, sodium tartarate, sodium acetate, sodium carbonate, sodium polyphosphate, potassium polyphosphate, sodium pyrophosphate, potassium pyrophosphate, disodium hydrogen phosphate, dibasic sodium phosphate, trisodium phosphate, tripotassium phosphate, sodium acetate, potassium metaphosphate, magnesium oxide, magnesium carbonate, magnesium silicate, calcium acetate, calcium glycerophosphate, calcium chloride, calcium hydroxide, calcium lactate, calcium carbonate, calcium bicarbonate, and other calcium salts. Some buffering agents also impart effervescent qualities when a powder is compounded into a liquid. In some embodiments, the colchicine described herein, when compounded into a liquid form, comprises a buffering agent.

Preservatives include anti-microbials, anti-oxidants, and agents that enhance sterility. Exemplary preservatives include ascorbic acid, ascorbyl palmitate, benzyl alcohol, BHA, BHT, citric acid, erythorbic acid, fumaric acid, malic acid, propyl gallate, sodium ascorbate, sodium benzoate, sodium bisulfate, sodium metabisulfite, sodium sulfite, parabens (methyl-, ethyl-, butyl-), benzoic acid, potassium sorbate, and vanillin. In some embodiments, the colchicine described herein, when compounded into a liquid form, comprises a preservative.

Sweeteners or sweetening agents include any compounds that provide a sweet taste to make the product more palatable. This includes natural and synthetic sugars, natural and artificial sweeteners (e.g., sucralose), natural extracts and any material that initiates a sweet sensation in a subject. In some embodiments, the colchicine described herein, when compounded into a liquid form, comprises a sweetener. In other embodiments, sweeteners in liquid form are used to solvate or dissolve the colchicine described herein.

Sugars illustratively include glucose, fructose, sucrose, xylitol, tagatose, maltitol, isomaltulose, lactitol, sorbitol, mannitol, erythritol, trehalose, maltodextrin, polydextrose, and the like. Other sweeteners include glycerin, inulin, maltol, acesulfame and salts thereof, e.g., acesulfame potassium, alitame, aspartame, neotame, sodium cyclamate, saccharin and salts thereof, e.g., saccharin sodium or saccharin calcium, neohesperidin dihydrochalcone, stevioside, thaumatin, and the like. Sweeteners can be used in the form of crude or refined products such as hydrogenated starch hydrosylates, maltitol syrup, high fructose corn syrup, and as branded proprietary blend products. Sweeteners can be used singly or combinations of two or more. Suitable concentrations of different sweeteners can be selected based on published information, manufacturers' data sheets, and by routine testing. In certain instances, an above-described flavored solution component is used to solvate or dissolves colchicine described herein.

In another embodiment, the liquid form comprises a flavoring agent or flavorant to enhance the taste or aroma of the solution component used to solvate or dissolve the colchicine described herein. Suitable natural or synthetic flavoring agents can be selected from standard reference books, such as Remington: The Science and Practice of Pharmacy (2000) and Fenaroli's Handbook of Flavor Ingredients (1994). Non-limiting examples of suitable natural flavors, some of which can be readily simulated with synthetic agents or combinations thereof, include almond, anise, apple, apricot, banana, blackberry, blackcurrant, blueberry, caramel, cherry, chocolate, cinnamon, cranberry, grape, lemon, lime, orange, peppermint, pineapple, raspberry, spearmint, strawberry, vanilla, etc. Also useful, particularly where the composition is intended primarily for pediatric use is tutti-frutti or bubble gum flavor, a compounded flavoring agent based on fruit flavors. Presently, preferred flavoring agents include bubble gum, strawberry, cherry, grape, orange, peppermint, and vanilla. In some embodiments, the resultant liquid form from the colchicine described herein comprises a Flavor Cherry 825.662 flavoring agent. Flavoring agents may be used singly or in combinations of two or more.

In further embodiments, the resultant liquid form from the colchicine described herein comprises a coloring agent for identity and/or aesthetic purposes. Suitable coloring agents approved by the U.S. Food and Drug Administration (FDA) include FD&C Red No. 3, FD&C Red No. 20, FD&C Red No. 40, FD&C Yellow No. 6, FD&C Blue No. 2, D&C Green No. 5, D&C Orange No. 5, D&C Yellow No. 10, caramel, ferric oxide and mixtures thereof.

In further embodiments, the resultant liquid form from the colchicine described herein comprises a thickening agent Thickening agents include, but are not limited to xanthan gum.

In some embodiments other flavoring agents, buffering systems, and preservatives may be used. The solution is formulated to inhibit growth of bacteria, mold, and yeast for storage at room temperature and ambient conditions.

In some embodiments, the liquid formulation is by % w/v can be found in Table 1. In other embodiments, the formulation includes 0.2-0.4% w/v of benzyl alcohol, 0.1-0.3% w/v of anhydrous citric acids, 0.005-0.025% w/v of colchicine, 0.005-0.02% w/v of FD&C Red No. 40, 0.8-1.6% w/v or dibasic sodium phosphate, heptahydrate, 0.75-0.15% w/v of flavor cherry 825.662, 2-8% w/v of propylene glycol, 2-10% glycerin, 0.1-0.2% w/v of sucralose, 0.1-0.2% w/v of xanthan gum, and water. In other embodiments, the formulation includes 0.28-3.2 or 0.3% w/v of benzyl alcohol, 0.2% w/v of anhydrous citric acids, 0.012% w/v of colchicine, 0.01% w/v of FD&C Red No. 40, 1.2% w/v or dibasic sodium phosphate, heptahydrate, 0.125% w/v of flavor cherry 825.662, 5% w/v of propylene glycol, 0.15% w/v of sucralose, 0.15% w/v of xanthan gum, and water.

TABLE 1

Exemplary formulation

| Ingredient | % w/v |
|---|---|
| Benzyl Alcohol | 0.3 |
| Citric Acid, Anhydrous | 0.2 |
| Colchicine* | 0.012 |
| FD&C Red No. 40 | 0.01 |
| Dibasic Sodium Phosphate, Heptahydrate | 1.2 |
| Flavor Cherry 825.662 | 0.125 |
| Propylene Glycol | 5 |
| Glycerin | 5 |
| Sucralose | 0.15 |
| Xanthan Gum | 0.15 |
| Water | Q.S. |

*Calculated on the anhydrous, solvent free basis

Storage

The colchicine described herein is stable in various storage conditions including refrigerated, ambient, and accelerated conditions. Stable as used herein refers to the ability of an active agent to maintain activity under standard stability conditions. Standard stability conditions include relative humidity conditions along with the temperatures, 25 degrees C. 60% RH (RT), 30 C 65% RH (ICH), and 40 C 75% RH (accelerated), for example.

At refrigerated and ambient conditions, the liquid colchicine composition described herein in stable for at least 1 month, at least 2 months, at least 3 months, at least 6 months, at least 9 months, at least 12 months, at least 15 months, at least 18 months, and at least 24 months. At accelerated conditions, the colchicine solution described herein is stable for at least 1 month, at least 2 months, at least 3 months and at least 6 months. Accelerated conditions include temperatures that are above ambient levels. In some instances, an accelerated condition is at about 30° C., about 35° C., about 40° C., about 45° C., about 50° C., about 55° C., or about 60° C. Ambient conditions include temperature that is at ambient levels. In some instances, an ambient condition is at about 20° C., about 21° C., about 22° C., about 23° C., about 24° C., about 25° C., about 26° C., about 27° C., about 28° C., about 29° C., and about 30° C. Refrigerated conditions include temperature in typical refrigeration units (e.g. 5±3° C.). In some instances, a refrigerated condition is about 2° C., about 3° C., about 4° C., about 5° C., about 6° C., about 7° C., or about 8° C.

Liquid vehicles suitable for the colchicine described herein are selected for a particular oral liquid composition (e.g., solution, suspension, etc.) as well as other properties such as clarity, viscosity, compatibility with excipients, chemical inertness, palatability, odor, and color. Exemplary liquid vehicles include water, ethyl alcohol, glycerin, propylene glycol, syrup (e.g., sugar or other sweetener based, e.g., Ora-Sweet® SF sugar-free flavored syrup), juices (e.g., apple, orange, cranberry, cherry, tomato and the like), other beverages (e.g., tea, coffee, soft drinks, milk and the like), oils (e.g., olive, soybean, corn, mineral, castor and the like), and combinations or mixtures thereof. Certain liquid vehicles, e.g., oil and water, can be combined together to form emulsions. In some embodiments, water is used as a vehicle for a colchicine oral liquid. In other embodiments, propylene glycol is used as a vehicle for a colchicine oral liquid. For the liquid colchicine described herein, the solution component is used as the vehicle for a colchicine oral liquid.

The viscosity of the solution is an important component. In some embodiments the solution has a viscosity in the range of 40-800 cps. In other embodiments the solution has a viscosity of 80-250 cps.

The colchicine oral liquid compositions may be used for the treatment of diseases and conditions described herein. In addition, a method for treating any of the diseases or conditions described herein in a subject in need of such treatment involves administration of colchicine oral liquid compositions in therapeutically effective amounts to the subject. In some embodiments, the amount of a given colchicine oral liquid composition that corresponds to such an amount varies depending on factors such as the particular colchicine salt or form, disease condition and its severity, the identity (age, weight, sex) of the subject or patient in need of treatment, but can nevertheless be determined according to the particular circumstances surrounding the case, including, e.g., the specific agent being administered, the liquid composition type, the condition being treated, and the subject or patient being treated.

In further embodiments, the daily dosages appropriate for the colchicine oral liquid compositions described herein are from about 0.2 mg-1.5 mg/dose/day or in other embodiments 0.5 mg-1.5 mg/dose/day. In one embodiment, the daily dosage appropriate for the colchicine liquid compositions is about 0.6-1.2 mg/dose/day.

The treatment of certain diseases or conditions (e.g., gout, FMF, cardiac disease etc.) in a patient or subject with a colchicine oral liquid composition described herein encompass additional therapies and treatment agents in some embodiments. Such additional therapies and treatment regimens include another therapy, e.g., antibiotics, for the treatment of the particular disease in some embodiments.

Unless defined otherwise, all technical and scientific terms used herein have the same meanings as commonly understood by one of ordinary skill in the art. Although any methods and materials similar or equivalent to those described herein can be used in the practice of testing of embodiments described herein, certain preferred methods, devices, and materials are now described.

As used herein and in the appended claims, the singular forms "a", "an", and "the" include plural reference unless the context clearly dictates otherwise. Thus, for example, reference to "an excipient" is a reference to one or more excipients and equivalents thereof known to those skilled in the art, and so forth.

The term "about" is used to indicate that a value includes the standard level of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or". The terms "comprise", "have", and "include" are open-ended linking verbs. Any forms or tenses of one or more of these verbs "comprises," "comprising," "has," "having," "includes," and "including" are also open-ended. For example, any method that "comprises," "has" or "includes" one or more steps is not limited to possessing only those one or more steps and also covers other unlisted steps.

"Optional" or "optionally" may be taken to mean that the subsequently described structure, event or circumstance may or may not occur, and that the description includes instances where the events occurs and instances where it does not.

As used herein, the term "therapeutic" means an agent utilized to treat, combat, ameliorate, prevent or improve an unwanted condition or disease of a patient. In some embodiments, a therapeutic agent such as oral colchicine is directed to the treatment and/or the amelioration of, reversal of, or stabilization of the symptoms of gout, familial Mediterranean fever (FMF), pericarditis, Behçet's disease, atrial fibrillation, amyloidosis, calcium pyrophosphate deposition disease (pseudogout), cirrhosis of the liver, sarcoid arthritis, and inflammatory diseases described herein.

"Administering" when used in conjunction with a therapeutic means to administer a therapeutic systemically or locally, as directly into or onto a target tissue, or to administer a therapeutic to a patient whereby the therapeutic positively impacts the tissue to which it is targeted. Thus, as used herein, the term "administering", when used in conjunction with an oral colchicine composition, can include, but is not limited to, providing an oral colchicine composition into or onto the target tissue; providing an oral colchicine composition systemically to a patient by, e.g., oral administration whereby the therapeutic reaches the target tissue or cells. "Administering" a composition may be accomplished by injection, topical administration, and oral administration or by other methods alone or in combination with other known techniques.

As used herein, the terms "patient," "subject" and "individual" are intended to include living organisms in which certain conditions as described herein can occur. Examples include humans, monkeys, cows, sheep, goats, dogs, cats, mice, rats, and transgenic species thereof. In a preferred embodiment, the patient is a primate. In certain embodiments, the primate or subject is a human. In certain instances, the human is an adult. In certain instances, the human is child. In certain instances, the human is elderly. In other instances, the human is 65 years of age or older. Other examples of subjects include experimental animals such as mice, rats, dogs, cats, goats, sheep, pigs, and cows. By "pharmaceutically acceptable", it is meant the carrier, diluent or excipient must be compatible with the other ingredients of the formulation and not deleterious to the recipient thereof.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

A "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reversing the pathology and/or symptomatology).

The terms "treat," "treated," "treatment," or "treating" as used herein refers to both therapeutic treatment in some embodiments and prophylactic or preventative measures in other embodiments, wherein the object is to prevent or slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. A prophylactic benefit of treatment includes prevention of a condition, retarding the progress of a condition, stabilization of a condition, or decreasing the likelihood of occurrence of a condition. As used herein, "treat," "treated," "treatment," or "treating" includes prophylaxis in some embodiments.

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1: Formulations

TABLE 2

Liquid Colchicine Formulation

| Ingredient | % w/v |
| --- | --- |
| Benzyl Alcohol | 0.3 |
| Citric Acid, Anhydrous | 0.2 |
| Colchicine* | 0.012 |
| FD&C Red No. 40 | 0.01 |
| Dibasic Sodium Phosphate, Heptahydrate | 1.2 |
| Flavor Cherry 825.662 | 0.125 |
| Propylene Glycol | 5 |
| Glycerin | 5 |
| Sucralose | 0.15 |
| Xanthan Gum | 0.15 |
| Water | Q.S. |

*Calculated on the anhydrous, solvent free basis

In some embodiments, the oral liquid formulation includes: the 0.3% w/v of benzyl alcohol, 0.2% w/v of anhydrous citric acids, 0.012% w/v of colchicine, 0.01% w/v of FD&C Red No. 40, 1.2% w/v or dibasic sodium phosphate, heptahydrate, 0.125% w/v of flavor cherry 825.662, 5% w/v of propylene glycol, 0.15% w/v of sucralose, 0.15% w/v of xanthan gum, and water as seen in Table 2.

Example 2: Stability

Colchicine has been shown to be unstable at room temperature in solution. An article published in Drug Development and Industrial Pharmacy, 15(11), 1905-1909 (1989) by Habib, et. al., investigated the stability of colchicine and showed that there is photodegradation of colchicine in solution, especially in the presence of glycerin, (up to a 50% loss). The additives, such as lithium carbonate, p-aminobenzoic acid, and uric acid, used in this study to try and prevent the degradation of the colchicine are not acceptable excipients for an oral solution. Furthermore, these ingredients did not prevent the degradation of the colchicine. The stability studies described in this paper were conducted over hours, which would not yield a pharmaceutically acceptable product.

Colchicine solutions are used in biological studies for cellular assays. Companies like BI (Biological Industries) sell a colchicine solution in a cellular buffering agent. The storage conditions are 2-8° in order to prevent degradation, as these types of solutions are not stable at room temperature. Furthermore, the safety information/MSDS for the buffers used to make these solutions state that it is harmful if ingested.

The product information from various suppliers of colchicine crystalline powder for laboratory use state that colchicine should be stored at freezing temperatures or refrigeration to maintain stability. Cayman Chemical's product information regarding colchicine states that they do not recommend storing an aqueous solution made from their crystalline colchicine powder for more than one day. Sigma product information on colchicine says to store any made solutions between 2-8° for stability purposes. Furthermore these product information sheets are for the colchicine crystalline powder and any solutions described are not only not stable at room temperature for any period of time, but are not solutions for oral consumption, as they are made with buffers and solvents that are not for human consumption, such as DPBS, benzene, and chloroform. These solutions are for cellular assays in a laboratory setting.

The colchicine injections for IV administration are made in single unit doses, and the label and package inserts for these products specifically state that the colchicine injections are for intravenous use only.

The colchicine compounded solutions for veterinary purposes are for immediate use, and there is no stability data generated on these types of products. As the prior art shows, colchicine solutions currently manufactured are not stable at room temperature for long term, and furthermore none of the solutions described could be used for human oral consumption.

Surprisingly, a stable oral colchicine solution that is even stable in the presence of glycerin has been developed according to the invention. The colchicine solution is formulated and assayed for colchicine levels. Stability of the claimed formulation was tested at room temperature, 30° C., and 40° C. and assayed for the colchicine. Results can be found in Table 3 below. Table 4 shows further stability data up through 6 months. The fact that the oral solution was so stable after 6 months at an accelerated temperature (40 degrees Celsius, which corresponds to 24 months at room temperature) was quite surprising. Solutions of colchicine for oral administration to humans have not been developed because they were believed to be too unstable. The data presented herein show for the first time that an oral colchicine solution can remain stable with minimal degradants and thus have a long shelf life consistent with commercial formulations.

TABLE 3

Stability Results of Colchicine Solution (% Label Claim)

| Sample | Result |
| --- | --- |
| API (colchicine drug substance)* | 91.8% |
| 3.5 months @ 5° | 92.3% |
| 3 months @ 25° ± 2° C. 60% ± 5% RH(RT) | 92.6% |
| 3 months @ 30° ± 2° C. 65% ± 5% RH(ICH) | 91.3% |
| 3 months @ 40° ± 2° C. 75% ± 5% RH(ACC) | 91.1% |

*Calculated on the anhydrous, solvent-free basis

TABLE 4

Stability Report for Colchicine Solution, 0.12 mg/mL

| Test Conditions | Initial | 1 Month | 2 Months | 3 Months | 6 Months |
| --- | --- | --- | --- | --- | --- |
| 25° C./60% RH | 98.1% | — | 96.7% | 97.3% | 96.7% |
| 30° C./65% RH | 98.1% | — | 96.8% | 96.5% | 96.6% |
| 40° C./75% RH | 98.1% | 96.6% | 97.0% | 96.7% | 95.1% |

These results show that there is no loss of colchicine from the initial raw API used and under all conditions after 6 months. These results show that the colchicine solution of the invention is stable, even at high temperatures. The colchicine does not degrade over time and under accelerated conditions. The results were calculated on an as is basis. The colchicine solution in Table 4 was packaged in a 190 mL HDPE bottle and assayed by HPLC cUSP.

These results show the percent of label claim of colchicine in the solution of the invention. The label claim of the liquid solution is 0.12 mg/ml and the assay results of the active ingredient are reported as percent of label claim. For instance, the label claim of an exemplary colchicine solution of the invention is 0.12 mg/ml. The FDA requirement for stability results for drugs is 90-110% label claim. These results show that colchicine was not degraded over time under accelerated conditions as well as at room temperature, which is surprising based on the prior art.

The pH of the liquid solution was evaluated (Table 5). The results show that the solution maintained a stable pH at accelerated conditions as well at room temperature.

TABLE 5

Evaluation of pH of Colchicine Oral Solution (Initial pH = 6.6)

| Condition | 1 month | 2 months | 3 months |
| --- | --- | --- | --- |
| RT | 6.48 | 6.61 | 6.59 |
| 30° | 6.59 | 6.57 | 6.60 |
| 40° | 6.49 | 6.59 | 6.57 |

A desirable range of pH includes 6.2-7.2. In some embodiments the pH range is 6.3-6.7.

Tables 6 and 7 below show data from USP antimicrobial preservatives effectiveness tests. The product tested in both cases met the requirements of the Current USP for Oral Products (Category 3 Products).

TABLE 6

| | Initial | Day 14 | | Day 28 | |
| --- | --- | --- | --- | --- | --- |
| Test Organism | Inoculum/ml | CFU/ml | Log red (% red) | CFU/ml | Log red (% red) |
| S. aureus ATCC #6538 | $6.1 \times 10^5$ | <10 | >4 (>99.99) | <10 | >4 (>99.99) |
| E. coli ATCC #8739 | $5.8 \times 10^5$ | $1.98 \times 10^4$ | 1.47 (96.59) | $1.46 \times 10^3$ | 2.60 (>99.75) |
| Ps. aeruginosa ATCC #9027 | $8.6 \times 10^5$ | <10 | >4 (>99.99) | <10 | >4 (>99.99) |
| C. albicans ATCC #10231 | $3.5 \times 10^5$ | $6.0 \times 10^3$ | 1.77 (98.29) | <10 | >4 (>99.99) |
| A. brasiliensis ATCC #16404 | $3.5 \times 10^5$ | $1.1 \times 10^2$ | 3.50 (99.97) | <10 | >4 (>99.99) |

TABLE 7

| | Initial | Day 14 | | Day 28 | |
| --- | --- | --- | --- | --- | --- |
| Test Organism | Inoculum/ml | CFU/ml | Log red (% red) | CFU/ml | Log red (% red) |
| S. aureus ATCC #6538 | $6.1 \times 10^5$ | $5.4 \times 10^3$ | 2.05 (99.11) | <10 | >4 (>99.99) |
| E. coli ATCC #8739 | $5.8 \times 10^5$ | $6.5 \times 10^1$ | 3.95 (99.99) | <10 | >4 (>99.99) |
| Ps. aeruginosa ATCC #9027 | $8.6 \times 10^5$ | <10 | >4 (>99.99) | <10 | >4 (>99.99) |
| C. albicans ATCC #10231 | $3.5 \times 10^5$ | $4.6 \times 10^2$ | 2.88 (99.87) | <10 | >4 (>99.99) |
| A. brasiliensis ATCC #16404 | $3.5 \times 10^5$ | $1.1 \times 10^2$ | 3.50 (99.97) | <10 | >4 (>99.99) |

Example 3: Colchicine Assay

This example presents the results of the evaluation of the application of the current USP Official (12/1/15-4/30/16) Monograph for Colchicine/Colchicine Injection (Assay) for Colchicine Oral Liquid 0.12 mg/mL. Evaluation included demonstration of system suitability, specificity for placebo and potentially interfering individual placebo components, and analysis of a sample preparation. The analysis was performed and documented within QCL project G8968.

Table 8, below, shows the sample materials that were used for the evaluation.

TABLE 8

Sample Materials

| Material Description | Lot # |
|---|---|
| Colchicine Oral Liquid, 0.12 mg/mL Formula 0090A-1 | 011416B |
| Colchicine Oral Liquid Placebo Formula 0090A-1-PI | 011416A |
| Colchicine, USP API (Indena) | 30670/H |
| FD&C Red No. 40 | 47943 |
| Flavor Cherry 825.662 FONA | S1528930 |
| Benzyl Alcohol Sigma-Aldrich | SHBD7983V |

The current USP Assay method for Colchicine Injection refers to the Assay method described in the monograph for Colchicine drug substance. The method employs an isocratic reverse phase separation with stationary phase L7 (C8) and UV detection at 254 nm with a 20 μL injection volume. The sample was prepared at a target concentration of 6 μg/mL Colchicine and compared to an external standard prepared at the same concentration. For the purposes of evaluation, Colchicine API was used for preparation of the external standard. Standard solutions were prepared in duplicate by the dilution of 12 mg Colchicine API to 200.0 mL in 50:50 methanol:water diluent. 10.0 mL of the resulting stock standard was further diluted to 100.0 mL in diluent to a concentration of 6 μg/mL Colchicine working standard. For the preparation of the sample solution, 8.0 mL (equivalent to 0.96 mg Colchicine) of the oral liquid was diluted to 50.0 mL in diluent. 30.0 mL of the resulting solution was further diluted to 100.0 mL in diluent to a concentration of 6 μg/mL Colchicine working sample solution. The HPLC method parameters are summarized in Table 9 and example chromatography is provided in FIG. 1.

TABLE 9

HPLC Parameters

| | Parameter |
|---|---|
| Mobile Phase | 45:55 0.5M monobasic potassium phosphate:methanol, pH 5.5 |
| Column | Waters SPHERISORB ® 5 μm C8 4.6 × 250 mm |
| Flow Rate | 1.1 mL/min |
| Column Temperature | 21° C. |
| Injection Volume | 20 μL |
| Detection | UV 254 nm |

All specified system suitability parameters were met and maintained throughout the analysis. A summary of system suitability requirements and results are provided in Table 10.

TABLE 10

System Suitability Parameters

| Parameter | Requirement | Result |
|---|---|---|
| Column efficiency (Theoretical Plates) | NLT 4500 | 7640 |
| Retention Time - Colchicine | 5.5-9.5 minutes | 8.8 minutes |
| RSD Colchicine Area | NMT 2% | 0.0% |
| Standard Check Agreement | 98.0-102.0% | 99.6% |

Colchicine Oral Liquid, 0.12 mg/mL, Formula 0090A-1, and the liquid placebo includes ingredients at the concentrations shown in Table 5. Placebo and ingredients with the potential for UV absorptivity and chromatographic interference were examined (Table 11).

TABLE 11

| Ingredient % | % w/v | Potential for Interference (Y/N) |
|---|---|---|
| Benzyl Alcohol | 0.3 | Y |
| Citric Acid, Anhydrous | 0.2 | N |
| Colchicine | 0.012* | — |
| FD&C Red No. 40 | 0.01 | Y |
| Dibasic Sodium Phosphate, Heptahydrate | 1.2 | N |
| Flavor Cherry 825.662 | 0.125 | Y |
| Glycerin USP (99.7%) | 5.0 | N |
| Propylene Glycol | 5.0 | N |
| Sucralose | 0.15 | N |
| Xanthan Gum | 0.15 | N |
| Water | Q.S. | N |

*Calculated on the anhydrous, solvent free basis

Figure 2:
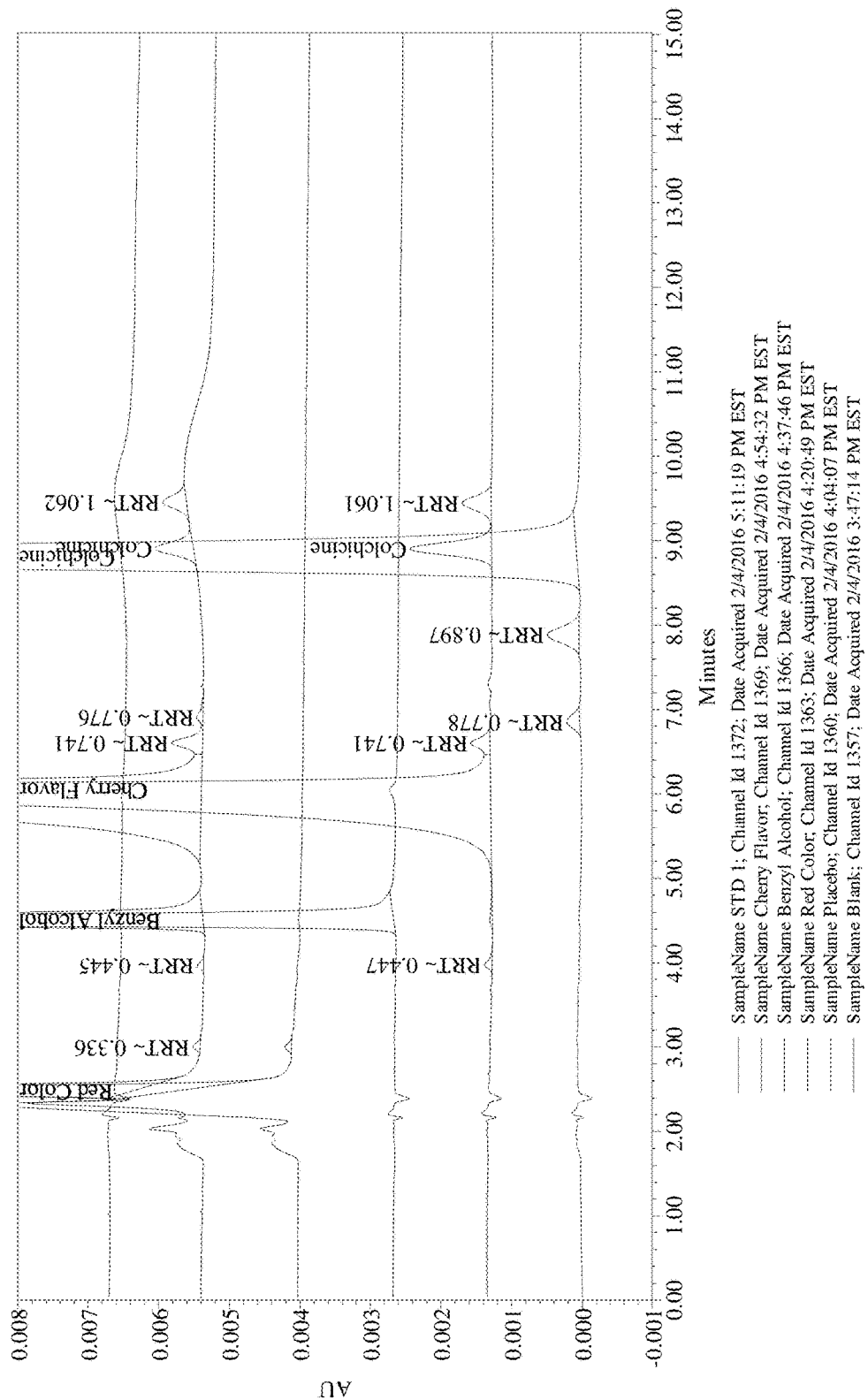
FIG. 2 depicts a chromatograph of an exemplary liquid oral colchicine solution. Diluent blank, placebo, red color, benzyl alcohol, flavor cherry, and colchicine standard are shown from top to bottom.

The placebo formulation and individual ingredients benzyl alcohol, FD&C Red No. 40, and Flavor Cherry 825.662 were prepared at nominal (100% of target formulation) concentrations in diluent. An overlay of the resulting peaks including chromatograms of diluent blank and colchicine standard are included in FIG. 2. Injections of benzyl alcohol and FD&C Red No. 40 resulted in single peaks that did not interfere at the retention time of colchicine. For the injection of Flavor Cherry 825.662, a primary peak and four minor secondary peaks were recorded. The secondary flavor related peak, at a retention time of 8.9 minutes, elutes at the approximate retention time of Colchicine (8.8 minutes), contributing interference at approximately 1.5% of the area response of a standard injection. Because the interfering peak completely co-elutes with colchicine, the assay calculation was performed by subtraction of the flavor related peak response obtained from injection of the placebo solution from the colchicine response of the sample injections.

The sample preparation was injected in duplicate, with the calculation performed against bracketing standard injections. The area response of the flavor related peak at retention time 8.9 minutes was subtracted from the area response of Colchicine in the sample injections. The assay results obtained was 99.1% of the labeled amount.

The USP Colchicine Assay method evaluated as described in this report is suitable for the routine assay of Colchicine in Colchicine Oral Liquid, 0.12 mg/mL. Minor interference due to the flavor cherry ingredient was mitigated by concurrent injection of placebo sample with area subtraction.

Example 4: Caco-2 Permeability of Colchicine

A Caco-2 study was conducted to compare the permeability of a colchicine solution of the invention to commercially available tablet and capsules. This study is an in vitro test that uses a gut cell line to measure permeability of the test articles. The results show that the colchicine oral solution has a similar permeability as the tablets and the capsules. These results indicate that the bioavailability of the colchicine solution in vivo will be similar to the tablets and the capsules.

The purpose of this study was to determine the permeability of Colchicine from different formulations for the purpose of BCS classification. This study was performed under non-GLP conditions. All work was performed with appropriate local health regulations and ethical approval. Colchicine monoisotopic mass is 399.17, and parent MW (free base) is 399.44.

Procedure:

Colchicine—Liquid—1 Bottle

Colchicine Liquid (1 mL equivalent to 300 μM Colchicine) was tested. The procedure included shaking the colchicine liquid bottle for a few seconds before using. The solution was then diluted to the final assay concentration.

Colchicine Tablets, USP+Sterile Water for Injection

Colchicine tablets, USP (equivalent to 0.6 mg or 300 μM colchicine) vial of 30 tablets were tested. 10 mL of sterile water was added for injection.

First, the cover from the colchicine vial was removed. The contents of 2 tablets were crushed into a fine powder. Then, 10 mL of sterile water was added, for injection, to the vial. The solution was then shaken well and sonicated for 10 minutes or until all of the powder was dissolved. Next, the solution was centrifuged for 10 minutes. The supernatant was retained and was diluted to the final assay concentration.

Colchicine Capsules+Sterile Water for Injection

Colchicine capsules (equivalent to 0.6 mg or 300 μM colchicine), vial of 100 capsules, were tested. 10 mL of sterile water was added for injection.

First, the cover from Colchicine vial was removed. 2 capsules were then carefully opened, and the contents were emptied into a vial. 10 mL of sterile water was added for injection to the vial. The well was then shaken and sonicated for 10 minutes or until all of the powder was dissolved. The product was then centrifuged for 10 minutes. The supernatant was retained and was diluted to the final assay concentration.

Methods

Mass Spectrometry Method Development

The signal was optimized for each compound by ESI positive or negative ionization mode. An MS2 scan or an SIM scan was used to optimize the fragmenter voltage and a product ion analysis was used to identify the best fragment for analysis, and the collision energy was optimized using a product ion or MRM scan. An ionization ranking was assigned indicating the compound's ease of ionization.

Analysis

Samples were analyzed by LC/MS/MS using an Agilent 6410 mass spectrometer coupled with an Agilent 1200 HPLC and a CTC PAL chilled autosampler, all controlled by MassHunter software (Agilent). After separation on a C18 reverse phase HPLC column (Agilent Zorbax 3.5 um, 2.1× 30 mm) using an acetonitrile-water gradient, peaks were analyzed by mass spectrometry using ESI ionization in MRM mode; Solution A contained $H_2O$ with 0.1% formic acid, and Solution B contained acetonitrile with 0.1% formic acid. Tables 12 and 13 show data regarding HPLC gradient and experimental conditions.

TABLE 12

HPLC Gradient

| Time (mm) | Flow rate (mL/min) | % A Mobile Phase | % B Mobile Phase |
|---|---|---|---|
| 0.37 | 1 | 98 | 2 |
| 1.88 | 1 | 5 | 95 |
| 2.06 | 1 | 5 | 95 |
| 2.14 | 1 | 98 | 2 |
| 3 | 1 | 98 | 2 |

TABLE 13

Caco-2 Permeability: Experimental Conditions

| Test Article | Test conc. | pH | Transport Direction | Reference compounds | Analytical method |
|---|---|---|---|---|---|
| Colchicine-Liquid | 10 μM | 5.7/7.4 | A→B | ranitidine | LC/MS/MS |
| Colchicine, USP-Tablets | | 6.5/7.4 | B→A | talinolol | |
| Colchicine-Capsules | | 7.4/7.4 | | metoprolol | |

Summary of Procedure:

Caco-2 cells were grown in tissue culture flasks and were trypsinized, suspended in medium, and the suspensions were applied to wells of a Millipore 96 well Caco-2 plate. The cells were allowed to grow and differentiate for three weeks, and fed at 2-day intervals.

For Apical to Basolateral (A→B) permeability, the test agent was added to the apical (A) side and amount of permeation was determined on the basolateral (B) side; for Basolateral to Apical (B→A) permeability, the test agent was added to the B side and the amount of permeation was determined on the A side. The A-side buffer contained 100 μM Lucifer yellow dye, in Transport Buffer (1.98 g/L glucose in 10 mM HEPES, 1× Hank's Balanced Salt Solution) at pH 5.7, 6.5, or 7.4, and the B-side buffer used was Transport Buffer, pH 7.4. Caco-2 cells were incubated with these buffers for 2 hours, and the receiver side buffer was removed for analysis by LC-MS/MS.

To verify the Caco-2 cell monolayers were properly formed, aliquots of the cell buffers were analyzed by fluorescence to determine the transport of the impermeable dye Lucifer Yellow. Any deviations from control values were reported.

Data expressed as permeability $(P_{app})$: $P_{app} = dQ/Dt/C_0A$.

dQ/dt: rate of permeation; $C_0$: initial concentration of test agent; A: area of monolayer. For bidirectional permeability studies, Efflux Ratio (RE): $R_e = P_{app}(B \to A)/P_{app}(A \to B)$. Table 14 shows mass spectrometry method development. Tables 15 and 16 show data regarding Caco-2 permeability data displaying a data summary and individual data from replicates, respectively.

Results

TABLE 14

Mass Spectrometry Method Development: MS/MS

| Test Article (API) | Monoisotopic Mass | ESI Polarization | Precursor m/2z | Product m/z | Ionization classification |
|---|---|---|---|---|---|
| Colchicine | 399.17 | Positive | 399.9 | 358.2 | 1 |

Ionization classification: 1 = Highly ionizable; 2 = Intermediately ionizable; 3 = Poorly ionizable m/z: Mass-to-Charge (or, mass-to-double charge) ratio of analyte

TABLE 15

Caco-2 Permeability Data Summary

| Test Article | Test conc. | pH (A/B) | mean A→B Papp (10−6 cm s−1) | mean B→A Papp (10−6 cm s−1) | Efflux ratio | Comment |
|---|---|---|---|---|---|---|
| ranitidine | 10 μM | 6.5/7.4 | 0.27 | 2.1 | 7.8 | Class III BCS |
| talinolol | 10 μM | 6.5/7.4 | 0.073 | 6.6 | 90.4 | P-gp efflux control |
| metoprolol | 10 μM | 6.5/7.4 | 13.7 | 27.2 | 2.0 | high BCS control (Class I BCS) |
| Colchicine-Liquid | 10 μM | 5.7/7.4 | 0.10 | 5.4 | 54.0 | |
| Colchicine, USP-Tablets | 10 μM | 5.7/7.4 | 0.12 | 4.9 | 40.8 | |
| Colchicine-Capsules | 10 μM | 5.7/7.4 | 0.15 | 5.2 | 34.7 | |
| Colchicine-Liquid | 10 μM | 6.5/7.4 | 0.16 | 5.4 | 33.8 | |
| Colchicine, USP-Tablets | 10 μM | 6.5/7.4 | 0.17 | 5.2 | 30.6 | |
| Colchicine-Capsules | 10 μM | 6.5/7.4 | 0.14 | 5.3 | 37.9 | |
| Colchicine-Liquid | 10 μM | 7.4/7.4 | 0.12 | 5.8 | 48.3 | |
| Colchicine, USP-Tablet | 10 μM | 7.4/7.4 | 0.13 | 5.8 | 44.6 | |
| Colchicine-Capsules | 10 μM | 7.4/7.4 | 0.18 | 6.4 | 35.6 | |

TABLE 16

Caco-2 Permeability: Individual Data from Replicates

| Test Article | pH (A/B) | Transport Direction | Papp (10−6 cm s−1) 1st replicate | 2nd replicate | 3rd replicate | Mean | A→B Post-Assay Recovery |
|---|---|---|---|---|---|---|---|
| Colchicine-Liquid | 5.7/7.4 | A→B | 0.10 | 0.10 | 0.10 | 0.10 | 61% |
| | | B→A | 5.2 | 5.2 | 5.4 | 5.1 | |
| | 6.5/7.4 | A→B | 0.19 | 0.13 | 0.16 | 0.16 | 63% |
| | | B→A | 5.6 | 5.1 | 5.5 | 5.4 | |
| | 7.4/7.4 | A→B | 0.13 | 0.13 | 0.091 | 0.12 | 64% |
| | | B→A | 5.3 | 6.1 | 6.1 | 5.7 | |
| Colchicine, USP-Tablets | 5.7/7.4 | A→B | 0.15 | 0.11 | 0.091 | 0.12 | 65% |
| | | B→A | 4.7 | 5.1 | 5.0 | 4.9 | |
| | 6.5/7.4 | A→B | 0.12 | 0.13 | 0.25 | 0.17 | 63% |
| | | B→A | 4.7 | 5.4 | 5.6 | 5.1 | |
| | 7.4/7.4 | A→B | 0.16 | 0.15 | 0.093 | 0.13 | 63% |
| | | B→A | 5.5 | 5.7 | 6.3 | 5.6 | |
| Colchicine-Capsules | 5.7/7.4 | A→B | 0.15 | 0.17 | 0.13 | 0.15 | 63% |
| | | B→A | 5.0 | 5.1 | 5.4 | 5.0 | |
| | 6.5/7.4 | A→B | 0.18 | 0.084 | 0.15 | 0.14 | 64% |
| | | B→A | 5.2 | 5.1 | 5.5 | 5.1 | |
| | 7.4/7.4 | A→B | 0.16 | 0.19 | 0.19 | 0.18 | 63% |
| | | B→A | 6.3 | 6.2 | 6.6 | 6.2 | |

Papp: apparent permeability rate coefficient

QC Criteria

Figure 3:
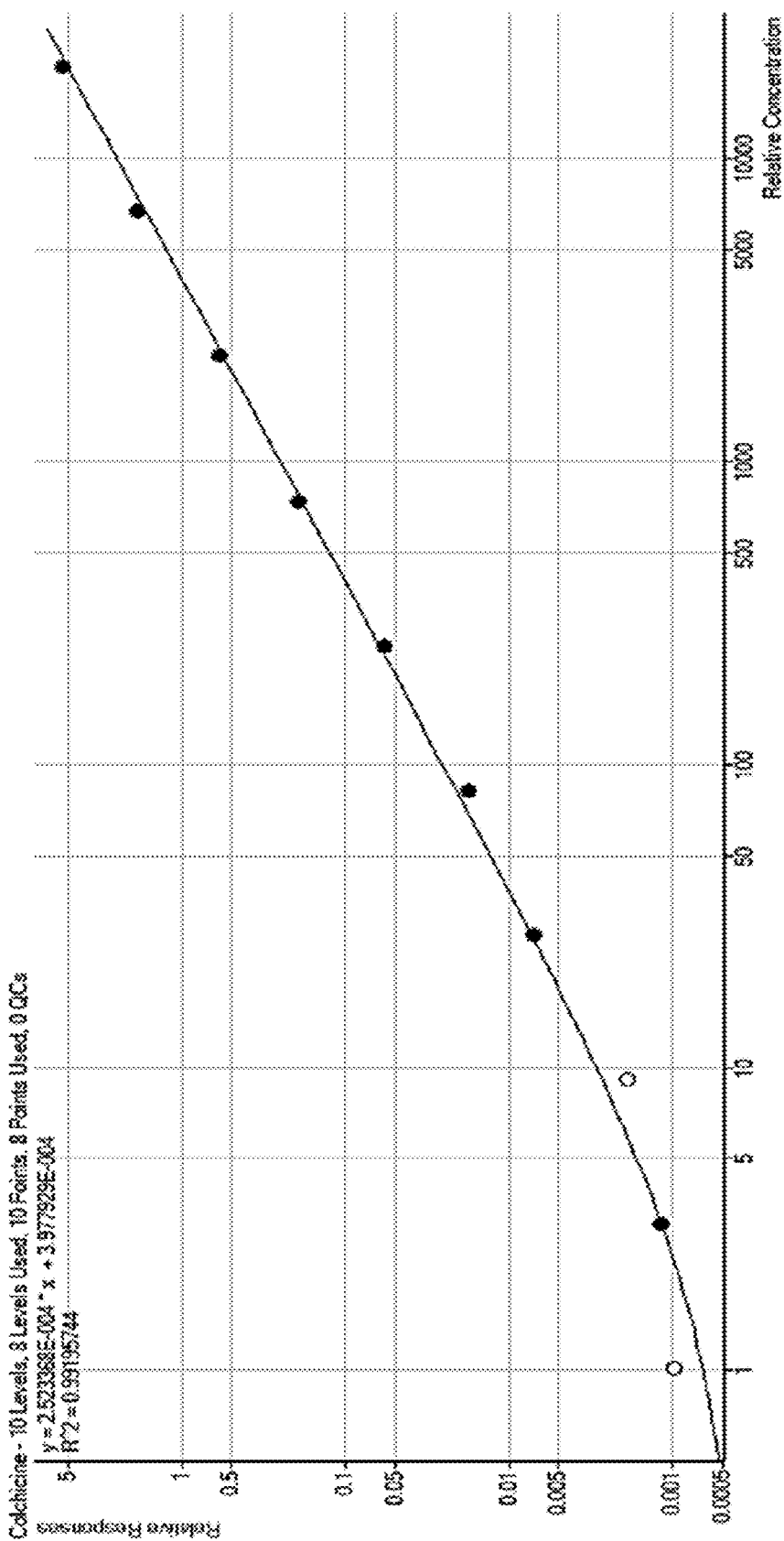
FIG. 3 shows the calibration curve of colchicine in Caco-2 transport buffer.

All wells utilized in this study passed QC criteria for epithelial monolayer integrity. All wells utilized exhibited Lucifer Yellow transport less than 2% (unless noted otherwise). All wells that were utilized in this assay exhibited TEER (Trans-Epithelial Electrical Resistance) readings greater than 1500 Ohms, also in accordance with QC criteria for acceptable monolayer integrity. FIG. 3 shows the calibration curve of colchicine in Caco-2 transport buffer.

BCS criterion classifies all 3 batches of Colchicine tested in this study as exhibiting low permeability across the pH ranges tested (5.7, 6.5, and 7.4). All 3 batches of Colchicine tested in this study (USP tablets, capsules, and liquid) exhibited a very similar permeability profile (i.e. low permeability with high efflux ratios and similar post-assay recovery levels).

The apparent permeability rate coefficients ($P_{app}$) for all 3 batches of Colchicine tested in this study (in the absorptive, A→B, transport direction) approximates only 1% (or less) of the Papp coefficient of the BCS high permeability control compound, metoprolol.

Figure 4:
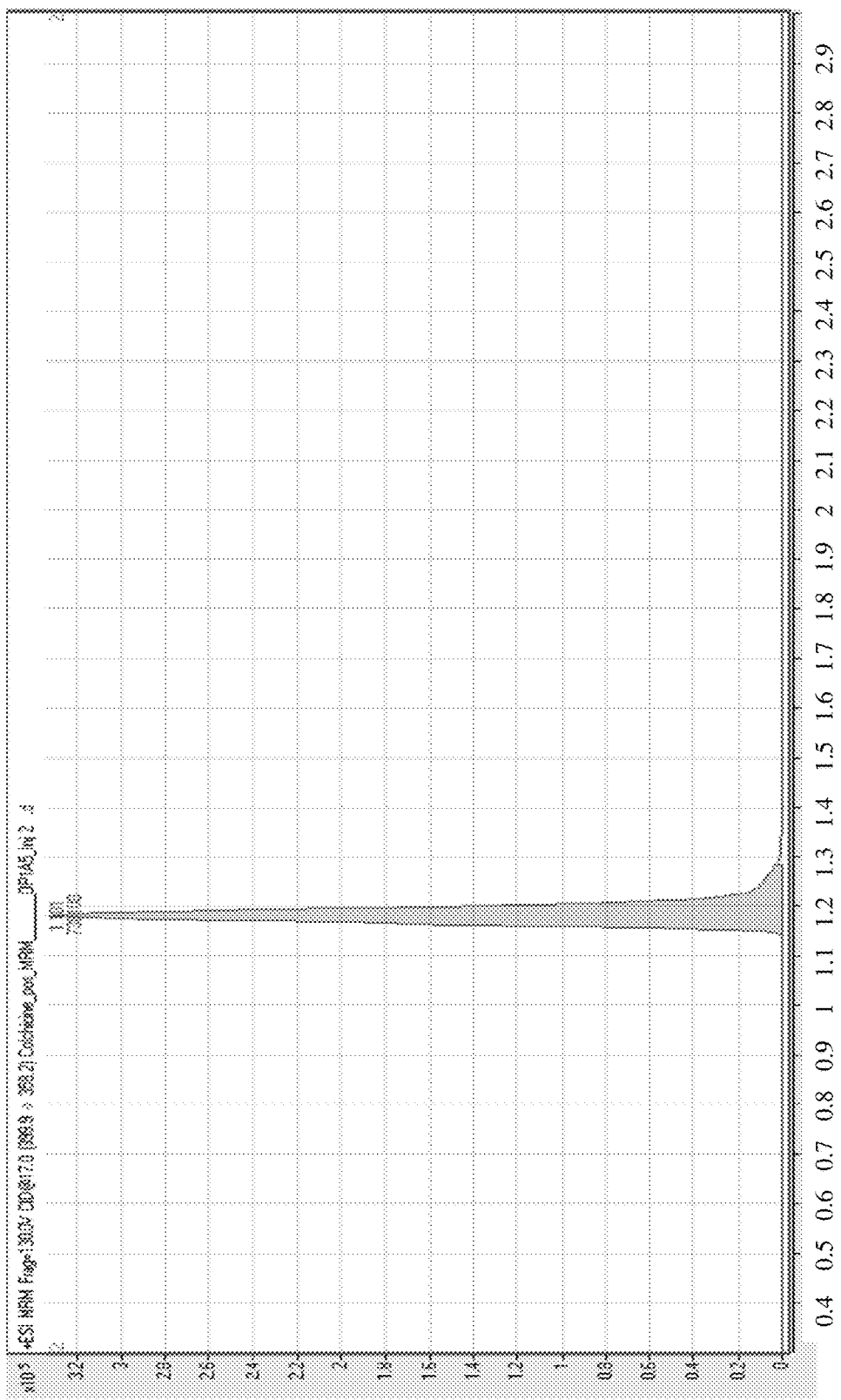
FIG. 4 shows a chromatogram of colchicine in Caco-2 buffer.
Figure 5A:
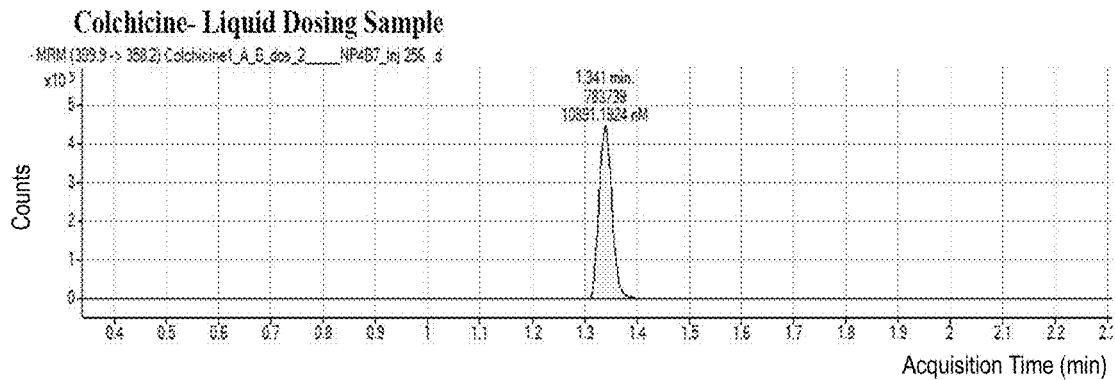
FIGS. 5A-5F show representative colchicine chromatograms.
Figure 5B:
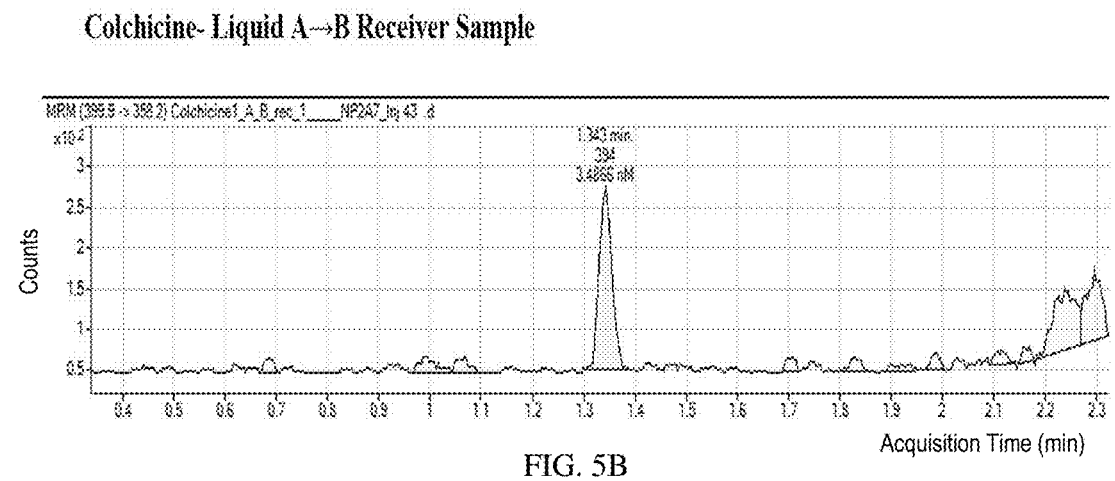
Figure 5C:
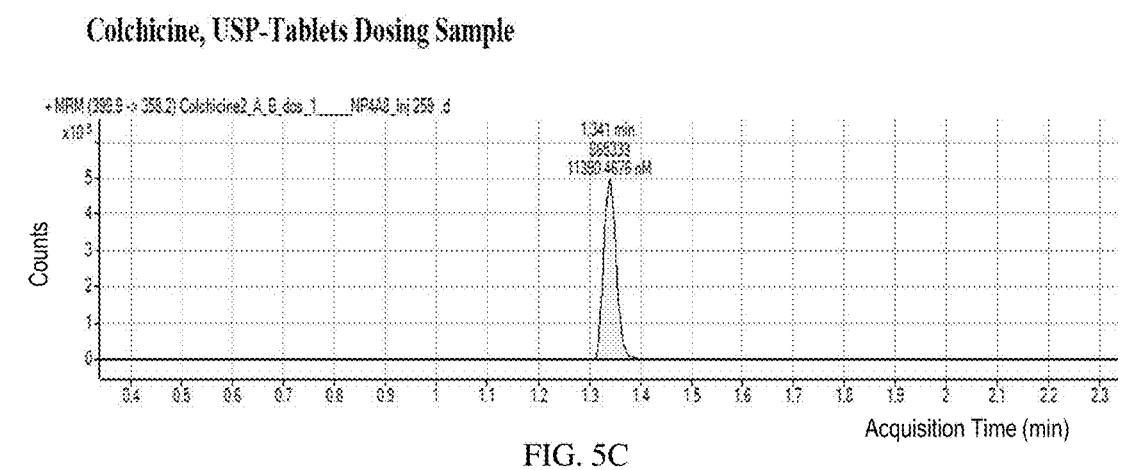
Figure 5D:
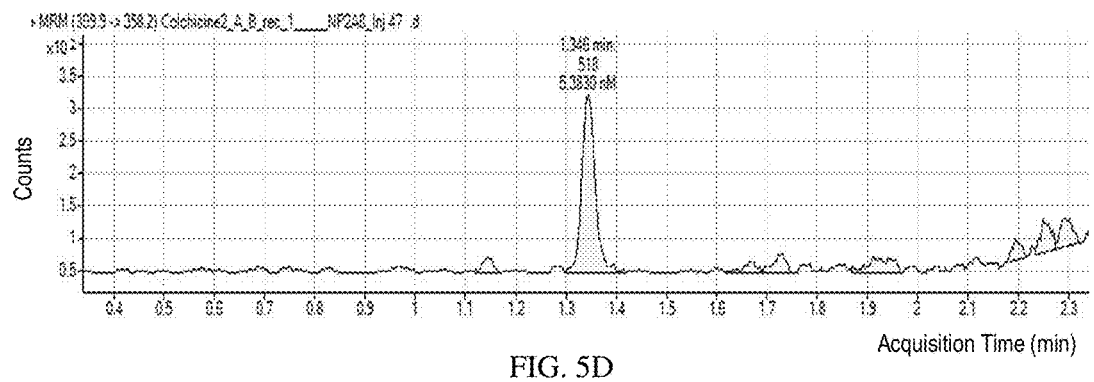
Figure 5E:
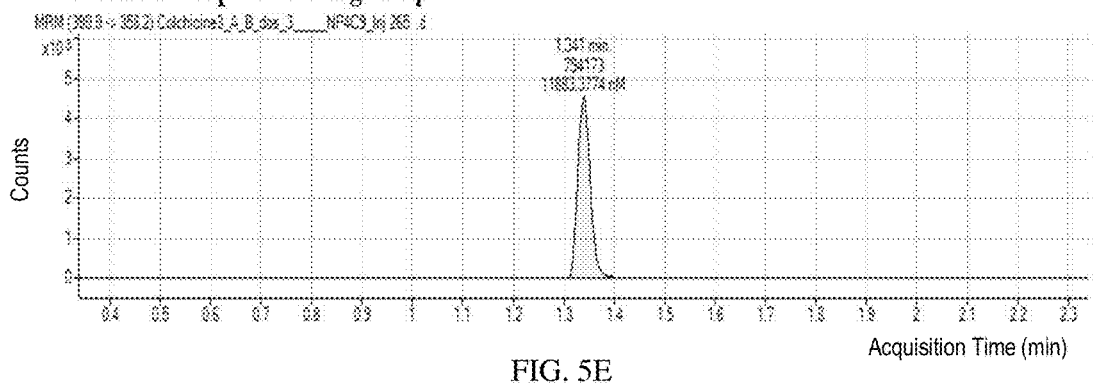
Figure 5F:
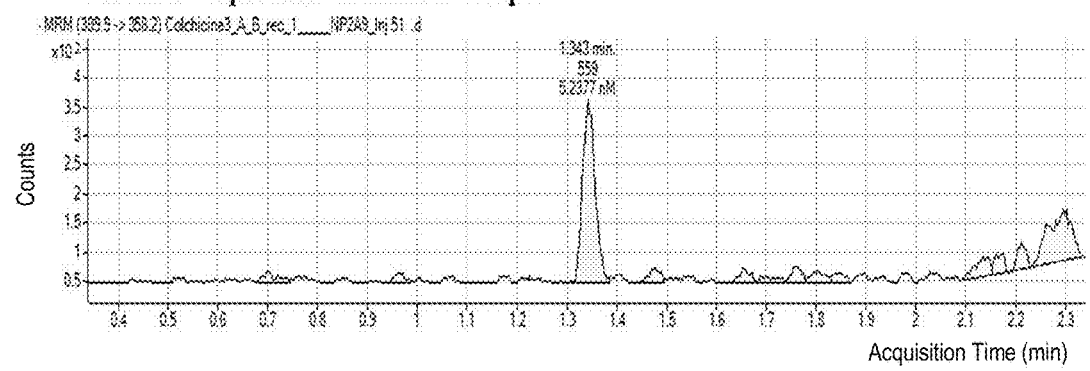

This value of 1% does not meet the 90% threshold of FDA criteria for BCS classification as high permeability. As a result, all 3 batches of Colchicine tested in this study are classified as exhibiting low permeability for BCS purposes. (Current EMA guidelines for BCS classification are 80% of the positive control for high permeability). FIG. 4 shows a colchicine chromatograms in Caco-2 buffer. Table 17 shows the MRM transition for colchicine. Table 18 shows cumulative colchicine oral solution data at 25° C.±2° C./60%±5% RH, which has been stable for at least 3 months. Table 19 shows the cumulative colchicine oral solution data at 40° C.±2° C./75%±5% RH, which has been stable for at least 3 months. It is mandatory to add a suitable preservative to non-sterile solutions, it maintain microbiological integrity for the remainder of the shelf-life. The preservative should also be stable to maintain its anti-microbial activity. Benzyl alcohol, a preservative in the colchicine oral solution tested in Tables 18 and 19, is stable and is compatible with colchicine as well as all excipients.

The data presented herein also shows that over a period of time the active drug-substance (colchicine) does not degrade more than the accepted limit and the each of the degradants does not exceed a certain threshold. No such information is available in the literature for liquid colchicine. As you can see, the data herein show that, fortunately, the degradants, after 3-month storage, even at 40° C./75% RH (indicative of stability to 24-month at room temperature), are either not detected or not quantifiable (very small quantity).

A liquid formulation of colchicine has been made for oral consumption which is stable, has a compatible and stable preservative, and under degrades minimally in longer-term storage conditions (well below the acceptable limit).

TABLE 17

MRM Transition for Colchicine: MS/MS Method Development

| Test Article | Mono-Isotopic Mass | ESI Polarization | Precursor m/z | Product m/z | Ionization Classification |
|---|---|---|---|---|---|
| Colchicine | 399.17 | Positive | 399.9 | 358.2 | 1 | m/z: mass-to-charge ratio of analyte
Ionization Classification: 1 = Highly Ionizable

TABLE 18

Cumulative Colchicine Oral Solution Data at 25° C. ± 2° C./60% ± 5% RH
Stability Data: Colchicine Oral Solution

| Batch No.: | PD16033 | Storage Condition: | 25° ± 2° C./60% ± 5% RH |
| | | Drug Substance Batch No.: | 31626/H |
| | | Container Closure: | 190-cc, Oblong, HDPE Bottles with 38-400 mm Auto-Loc CRC with a foil liner |

| Test Parameter Analytical Procedure | Acceptance Criteria | Results [Storage (Months)] | | | | |
|---|---|---|---|---|---|---|
| | | 0 | 1 | 2 | 3 | 6 |
| Description Organoleptic | A slightly hazy, red liquid with a cherry odor. | Conforms | Conforms | Conforms | Conforms | |
| pH USP <791> | 6.0 to 7.2 | 6.6 | 6.6 | 6.6 | 6.6 | |
| Density USP <841> | 1.00 to 1.04 g/mL at 25° C. | 1.02 | 1.02 | 1.02 | 1.02 | |
| Colchicine Assay In-house HPLC | 0.108 to 0.132 mg/mL (90.0 to 110.0% of label claim) | 99.3 | 100.0 | 100.0 | 99.8 | |
| Benzyl Alcohol Assay In-house HPLC | 2.4 to 3.6 mg/mL (80 to 120% of label claim) | 99 | 99 | 98 | 98 | |
| Related Substances In-house HPLC | | | | | | |
| β-lumicolchicine | NMT 1.0% | NT | NT | NT | ND | |
| γ-lumicolchicine | NMT 1.0% | NT | NT | NT | ND | |
| Colchiceine | NMT 1.0% | NT | NT | NT | < LOQ | |
| Any other individual unknown impurities | NMT 1.0% | NT | NT | NT | ND | |
| Total Impurities | NMT 5.0% | NT | NT | NT | < LOQ | |

HPLC: High Performance Liquid Chromatography
NMT: Not More Than
NLT: Not Less Than
NT: Not Tested (Testing not required by development specification.)

TABLE 19

Cumulative Colchicine Oral Solution Data at 40° C. ± 2° C./75% ± 5% RH
Stability Data: Colchicine Oral Solution

| Batch No.: | PD16033 | Storage Condition: | 40° ± 2° C./75% ± 5% RH |
| --- | --- | --- | --- |
| | | Drug Substance Batch No.: | 31626/H |
| | | Container Closure: | 190-cc, Oblong, HDPE Bottles with 38-400 mm Auto-Loc CRC with a foil liner |

| Test Parameter Analytical Procedure | Acceptance Criteria | Results [Storage (Months)] | | | | |
| --- | --- | --- | --- | --- | --- | --- |
| | | 0 | 1 | 2 | 3 | 6 |
| Description Organoleptic | A slightly hazy, red liquid with a cherry odor. | Conforms | Conforms | Conforms | Conforms | |
| pH USP <791> | 6.0 to 7.2 | 6.6 | 6.6 | 6.6 | 6.6 | |
| Density USP <841> | 1.00 to 1.04 g/mL at 25° C. | 1.02 | 1.02 | 1.02 | 1.02 | |
| Colchicine Assay In-house HPLC | 0.108 to 0.132 mg/mL (90.0 to 110.0% of label claim) | 99.3 | 99.2 | 99.6 | 97.4 | |
| Benzyl Alcohol Assay In-house HPLC | 2.4 to 3.6 mg/mL (80 to 120% of label claim) | 99 | 97 | 96 | 93 | |
| Related Substances In-house HPLC | | | | | | |
| β-lumicolchicine | NMT 1.0% | NT | NT | NT | ND | |
| γ-lumicolchicine | NMT 1.0% | NT | NT | NT | ND | |
| Colchiceine | NMT 1.0% | NT | NT | NT | < LOQ | |
| Any other individual unknown impurities | NMT 1.0% | NT | NT | NT | ND | |
| Total Impurities | NMT 5.0% | NT | NT | NT | < LOQ | |

HPLC: High Performance Liquid Chromatography
NMT: Not More Than
NLT: Not Less Than
NT: Not Tested (Testing not required by development specification.)

REFERENCES

Habib, M. J. et al (2008). "Influence of certain additives on the photostability of colchicine solutions." Drug Development and Industrial Pharm. 15(11):1905-1909.

Stewart, B. H. et al. (1995). "Comparison of Intestinal Permeabilities Determined in Multiple In Vitro and In Situ Models: Relationship to Absorption in Humans." Pharm. Res. 12:693-699.

Artursson, P. et al. (2001). "Caco-2 Monolayers in Experimental and Theoretical Predictions of Drug Transport." Adv. Drug Deliv. Rev. 46:27-43.

Yee, Shiyin (1997). "In Vitro Permeability across Caco-2 Cells (Colonic) Can Predict In Vivo (Small Intestinal) Absorption in Man—Fact or Myth." Pharm. Res 14(6): 763-766.

Yu, L. X. et al (2002). "Biopharmaceutics Classification System: The Scientific Basis for Biowaiver Extensions." Pharm Res. 19(7): 921-925.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A liquid solution suitable for oral administration comprising colchicine and a pharmaceutically acceptable solvent system comprised of water, buffering agents, and one or more agents selected from the group consisting of glycols, sweeteners, flavoring agents, preservatives, thickening agents, and dyes, wherein
the liquid solution is stable for 30 days to 24 months at ambient and refrigerated temperature conditions, wherein the liquid solution is comprised of the following components:

| ingredient | % w/v |
| --- | --- |
| benzyl alcohol | 0.2-0.4% |
| citric acid, anhydrous | 0.1-0.3% |
| colchicine | 0.01-1.0 mg/mL * |
| dibasic sodium phosphate heptahydrate | 0.8-1.6% |
| propylene glycol | 2-8% |
| glycerin | 2-10% |
| xanthan gum | 0.1-0.2% |
| water | Q.S. |

*Calculated on the anhydrous, solvent free basis.

2. The liquid solution of claim 1, wherein the pharmaceutically acceptable solvent system is comprised of one or more agents selected from the group consisting of water, propylene glycol, glycerin, benzyl alcohol, dibasic sodium phosphate heptahydrate, citric acid anhydrous, xanthan gum, sucralose, a dye, and a flavoring agent and/or taste enhancing agent.

3. The liquid solution of claim 1, wherein the pharmaceutically acceptable solvent system is comprised of the following components:

| Ingredient | % w/v |
| --- | --- |
| benzyl alcohol | 0.3 |
| citric acid, anhydrous | 0.2 |
| colchicine | 0.012* |
| FD&C red no. 40 | 0.01 |
| dibasic sodium phosphate heptahydrate | 1.2 |
| flavor cherry 825.662 | 0.125 |
| propylene glycol | 5 |
| glycerin | 5 |
| sucralose | 0.15 |
| xanthan gum | 0.15 |
| water | Q.S. |

*calculated on the anhydrous, solvent free basis.

4. The liquid colchicine solution of claim 1, wherein the solution is stable for 3 months to 12 months at accelerated conditions.

5. The liquid colchicine solution of claim 1, wherein the solution has a stable pH.

6. The liquid colchicine solution of claim 1, wherein the solution has a viscosity in the range of 40-800 cps.

7. The liquid colchicine solution of claim 1, wherein the solution is volume packaged 60 mL-473 mL.

8. The liquid colchicine solution of claim 1, wherein the pH is range is 6.2-7.2.

9. The liquid colchicine solution of claim 1, wherein the solution has less than 5% of total impurities.

10. The liquid colchicine solution of claim 1, wherein the solution has less than 0.5% of degradants.

11. The liquid colchicine solution of claim 1, wherein the degradants comprise β-lumicolchicine, γ-lumicolchicine, and/or colchiceine.

* * * * *